(12) United States Patent
Bartol et al.

(10) Patent No.: US 8,979,767 B2
(45) Date of Patent: *Mar. 17, 2015

(54) NEURAL MONITORING SYSTEM

(71) Applicant: Innovative Surgical Solutions, LLC, Southfield, MI (US)

(72) Inventors: Stephen Bartol, Windsor (CA); Christopher Wybo, Royal Oak, MI (US)

(73) Assignee: Innovative Surgical Solutions, LLC, Wixom, MI (US)

(*) Notice: Subject to any disclaimer, the term of this patent is extended or adjusted under 35 U.S.C. 154(b) by 141 days.

This patent is subject to a terminal disclaimer.

(21) Appl. No.: 13/676,809

(22) Filed: Nov. 14, 2012

(65) Prior Publication Data

US 2013/0072811 A1 Mar. 21, 2013

Related U.S. Application Data

(63) Continuation of application No. 12/856,970, filed on Aug. 16, 2010, now Pat. No. 8,343,079, which is a continuation-in-part of application No. 12/818,319, filed on Jun. 18, 2010, which is a continuation-in-part (Continued)

(51) Int. Cl.
 *A61B 5/11* (2006.01)
 *A61B 5/0488* (2006.01)
 *A61B 5/00* (2006.01)

(52) U.S. Cl.
 CPC ............ *A61B 5/1106* (2013.01); *A61B 5/0488* (2013.01); *A61B 5/1104* (2013.01); *A61B 5/4893* (2013.01); *A61B 5/6843* (2013.01); *A61B 5/4029* (2013.01); *A61B 5/4519* (2013.01); *A61B 5/1107* (2013.01); *A61B 2505/05* (2013.01); *A61B 2560/0276* (2013.01);

(Continued)

(58) Field of Classification Search
 CPC ............. A61B 5/0488; A61B 5/04884; A61B 5/4893; A61B 5/4029; A61B 5/4519; A61B 5/1104; A61B 5/7239
 USPC .......................................... 600/546, 554, 595
 See application file for complete search history.

(56) References Cited

U.S. PATENT DOCUMENTS 4,817,628 A * 4/1989 Zealear et al. ................. 600/554
5,284,153 A * 2/1994 Raymond et al. ............. 600/554

(Continued)

*Primary Examiner* — Sean Dougherty
*Assistant Examiner* — Michael C Stout
(74) *Attorney, Agent, or Firm* — Quinn Law Group, PLLC

(57) ABSTRACT

A neural monitoring system for determining a proximity between a stimulator and a nerve within an intracorporeal treatment area of a human subject includes a stimulator, a mechanical sensor, and a receiver. The stimulator is configured to extend within the intracorporeal treatment area and to provide an electrical stimulus therein. The mechanical sensor is configured to be placed in mechanical communication with the muscle and to generate a mechanomyography output signal corresponding to a sensed mechanical movement of the muscle. The receiver is configured to: receive the mechanomyography output signal from the mechanical sensor; receive an indication of a magnitude of the provided intracorporeal stimulus; determine a magnitude of acceleration of the muscle from the received mechanomyography output signal; and determine a proximity between the stimulator and the nerve from the magnitude of the provided intracorporeal stimulus and the magnitude of acceleration of the muscle.

14 Claims, 17 Drawing Sheets

Related U.S. Application Data of application No. 12/605,020, filed on Oct. 23, 2009, which is a continuation-in-part of application No. 12/040,515, filed on Feb. 29, 2008.

(60) Provisional application No. 60/980,996, filed on Oct. 18, 2007, provisional application No. 61/229,530, filed on Jul. 29, 2009, provisional application No. 61/108,214, filed on Oct. 24, 2008.

(52) U.S. Cl.
CPC ....... *A61B 2562/0219* (2013.01); *A61B 5/7239* (2013.01); *A61B 5/7217* (2013.01); *A61B 5/6828* (2013.01); *A61B 2560/0412* (2013.01)
USPC ............................. 600/554; 600/595; 600/546

(56) References Cited

U.S. PATENT DOCUMENTS

| | | | | |
|---|---|---|---|---|
| 5,284,154 | A * | 2/1994 | Raymond et al. | 600/554 |
| 5,533,515 | A * | 7/1996 | Coller et al. | 600/593 |
| 5,775,331 | A * | 7/1998 | Raymond et al. | 600/554 |
| 6,059,569 | A * | 5/2000 | Otsuka | 433/72 |
| 6,361,508 | B1 * | 3/2002 | Johnson et al. | 600/595 |
| 6,500,128 | B2 * | 12/2002 | Marino | 600/554 |
| 6,984,208 | B2 * | 1/2006 | Zheng | 600/438 |
| 7,216,001 | B2 * | 5/2007 | Hacker et al. | 607/63 |
| 7,959,577 | B2 * | 6/2011 | Schmitz et al. | 600/554 |
| 7,981,058 | B2 * | 7/2011 | Akay | 600/595 |
| 8,343,065 | B2 * | 1/2013 | Bartol et al. | 600/554 |
| 8,343,079 | B2 * | 1/2013 | Bartol et al. | 600/595 |
| 8,517,954 | B2 * | 8/2013 | Bartol et al. | 600/554 |
| 2002/0065481 | A1 * | 5/2002 | Cory et al. | 604/21 |
| 2004/0077969 | A1 * | 4/2004 | Onda et al. | 600/547 |
| 2004/0122341 | A1 * | 6/2004 | Walsh et al. | 600/591 |
| 2004/0230138 | A1 * | 11/2004 | Inoue et al. | 600/595 |
| 2004/0243018 | A1 * | 12/2004 | Organ et al. | 600/547 |
| 2005/0182454 | A1 * | 8/2005 | Gharib et al. | 607/48 |
| 2005/0240086 | A1 * | 10/2005 | Akay | 600/300 |
| 2005/0283204 | A1 * | 12/2005 | Buhlmann et al. | 607/48 |
| 2006/0020218 | A1 * | 1/2006 | Freeman et al. | 600/509 |
| 2006/0135888 | A1 * | 6/2006 | Mimnagh-Kelleher et al. | 600/595 |
| 2006/0270949 | A1 * | 11/2006 | Mathie et al. | 600/595 |
| 2007/0016097 | A1 * | 1/2007 | Farquhar et al. | 600/546 |
| 2007/0038155 | A1 * | 2/2007 | Kelly et al. | 600/595 |
| 2007/0265675 | A1 * | 11/2007 | Lund et al. | 607/41 |
| 2008/0064976 | A1 * | 3/2008 | Kelleher et al. | 600/546 |
| 2008/0064977 | A1 * | 3/2008 | Kelleher et al. | 600/546 |
| 2008/0065178 | A1 * | 3/2008 | Kelleher et al. | 607/99 |
| 2008/0071191 | A1 * | 3/2008 | Kelleher et al. | 600/554 |
| 2008/0287761 | A1 * | 11/2008 | Hayter et al. | 600/365 |
| 2008/0306363 | A1 * | 12/2008 | Chaiken et al. | 600/310 |
| 2008/0312560 | A1 * | 12/2008 | Jamsen et al. | 600/595 |
| 2009/0018610 | A1 * | 1/2009 | Gharib et al. | 607/48 |
| 2009/0062696 | A1 * | 3/2009 | Nathan et al. | 600/595 |
| 2009/0069709 | A1 * | 3/2009 | Schmitz et al. | 600/547 |
| 2009/0076336 | A1 * | 3/2009 | Mazar et al. | 600/300 |
| 2009/0105604 | A1 * | 4/2009 | Bertagnoli et al. | 600/546 |
| 2009/0124860 | A1 * | 5/2009 | Miles et al. | 600/202 |
| 2009/0171381 | A1 * | 7/2009 | Schmitz et al. | 606/167 |
| 2009/0177112 | A1 * | 7/2009 | Gharib et al. | 600/554 |
| 2009/0192403 | A1 * | 7/2009 | Gharib et al. | 600/546 |
| 2009/0192416 | A1 * | 7/2009 | Ernst et al. | 600/595 |
| 2009/0204016 | A1 * | 8/2009 | Gharib et al. | 600/546 |
| 2009/0209879 | A1 * | 8/2009 | Kaula et al. | 600/546 |
| 2009/0228068 | A1 * | 9/2009 | Buhlmann et al. | 607/48 |
| 2010/0010367 | A1 * | 1/2010 | Foley et al. | 600/546 |
| 2010/0063377 | A1 * | 3/2010 | Becker et al. | 600/407 |
| 2010/0076335 | A1 * | 3/2010 | Gharib et al. | 600/546 |
| 2010/0094143 | A1 * | 4/2010 | Mahapatra et al. | 600/486 |
| 2010/0152604 | A1 * | 6/2010 | Kaula et al. | 600/546 |
| 2010/0240002 | A1 * | 9/2010 | Halevy-Politch et al. | 433/72 |
| 2010/0292617 | A1 * | 11/2010 | Lei et al. | 600/595 |
| 2013/0072811 | A1 * | 3/2013 | Bartol et al. | 600/546 |
| 2013/0253364 | A1 * | 9/2013 | Bartol et al. | 600/546 |

* cited by examiner

NEURAL MONITORING SYSTEM

CROSS REFERENCE TO RELATED APPLICATIONS

This application is a continuation of and claims the benefit of priority from U.S. application Ser. No. 12/856,970, filed Aug. 16, 2010 ("the '970 application"), which is a continuation-in-part of and claims the benefit of priority from U.S. application Ser. No. 12/818,319, filed Jun. 18, 2010 ("the '319 application"), which is a continuation-in-part and claims the benefit of priority of U.S. application Ser. No. 12/605,020, filed Oct. 23, 2009 ("the '020 application"), which is a continuation-in-part and claims the benefit of priority of U.S. application Ser. No. 12/040,515 ("the '515 application"), filed Feb. 29, 2008, which claims the benefit of priority to U.S. Provisional Application No. 60/980,996 ("the '996 application"), filed Oct. 18, 2007. The '020 application further claims the benefit of priority from U.S. Provisional Application Nos. 61/108,214 ("the '214 application"), filed Oct. 24, 2008 and 61/229,530 ("the '530 application"), filed Jul. 29, 2009. The entire disclosures of the '970 application, '319 application, '020 application, the '515 application, the '996 application, the '214 application, and the '530 application are hereby incorporated by reference as though fully set forth herein.

BACKGROUND

The present disclosure relates generally to a neural monitoring device that may be capable of detecting the proximity of a nerve from an invasive stimulator, and monitoring for potential nerve injury during a surgical procedure. Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

SUMMARY

A neural monitoring system for determining a proximity between a stimulator and a nerve within an intracorporeal treatment area of a human subject includes a stimulator, a mechanical sensor, and a receiver. The stimulator is configured to extend within the intracorporeal treatment area and to provide an electrical stimulus therein. The mechanical sensor is configured to be placed in mechanical communication with the muscle and to generate a mechanomyography output signal corresponding to a sensed mechanical movement of the muscle. The receiver is configured to: receive the mechanomyography output signal from the mechanical sensor; receive an indication of a magnitude of the provided intracorporeal stimulus; determine a magnitude of acceleration of the muscle from the received mechanomyography output signal; and determine a proximity between the stimulator and the nerve from the magnitude of the provided intracorporeal stimulus and the magnitude of acceleration of the muscle. The system may further include a display device in communication with the receiver, that that the receiver is further configured to display an indication of the determined proximity to a user via the display device.

The receiver may be further configured to: compute a time derivative of an acceleration of the muscle from the mechanomyography output signal; compare the computed time derivative of acceleration to a jerk threshold; and indicate that the sensed mechanical movement of the muscle was induced by the provided intracorporeal stimulus if the computed time derivative of acceleration exceeds the jerk threshold. Additionally, the receiver may be configured to: compare the determined proximity to a proximity threshold; and provide an alert if the determined proximity is less than the proximity threshold and the computed time derivative of acceleration exceeds the jerk threshold.

A method of determining a proximity between a stimulator and a nerve within an intracorporeal treatment area of a human subject may include: providing an electrical stimulus within the intracorporeal treatment area from a stimulator configured to extend within the intracorporeal treatment area; receiving a mechanomyography output signal from a mechanical sensor in mechanical communication with the muscle, the mechanomyography output signal corresponding to a mechanical movement of the muscle sensed by the mechanical sensor; receiving an indication of a magnitude of the provided intracorporeal stimulus; determining a magnitude of acceleration of the muscle from the received mechanomyography output signal; and determining a proximity between the stimulator and the nerve from the magnitude of the provided intracorporeal stimulus and the magnitude of acceleration of the muscle.

DETAILED DESCRIPTION

Figure 1:
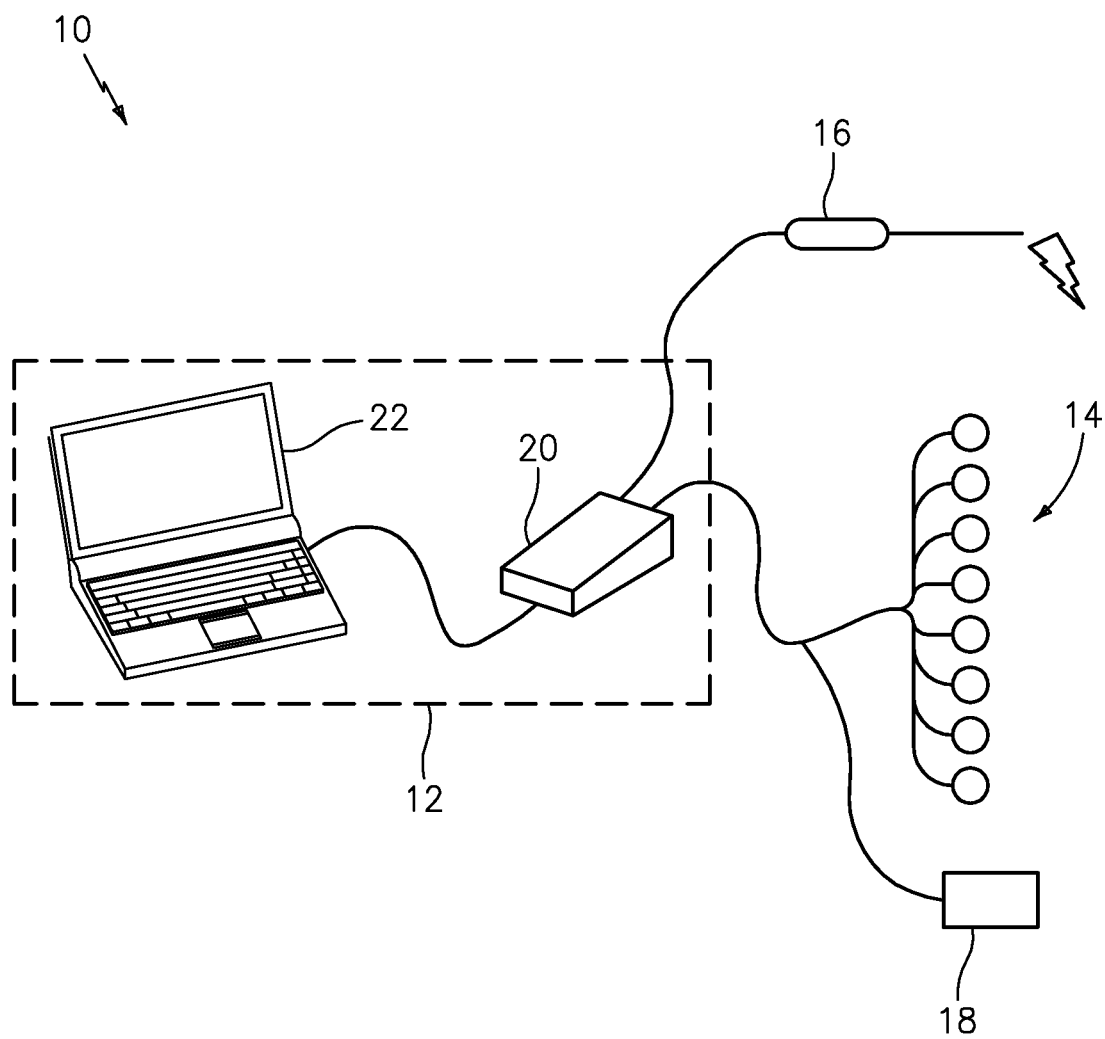
FIG. 1 illustrates an exemplary embodiment of a neural monitoring system.

Referring to the drawings, wherein like reference numerals are used to identify like or identical components in the various views, FIG. 1 illustrates an exemplary neural monitoring system 10 that includes a receiver 12 in communication with a plurality of sensing devices 14, a stimulator 16, and a ground patch 18. In an embodiment, the receiver 18 may include an interface 20 and a computing device 22. The computing device 22 may include a processor, memory, and a display, such as for example, a personal computer, tablet computer, personal digital assistant (PDA), or the like. The interface 20 may be configured to receive and present information from the one or more sensing devices 14 to the computing device 22, and may include, for example, communications circuitry, signal processing circuitry, and/or other associated interfacing circuitry. While shown as distinct components in FIG. 1, in an embodiment, the interface 20 may be an integral part of the computing device 22.

Figure 2:
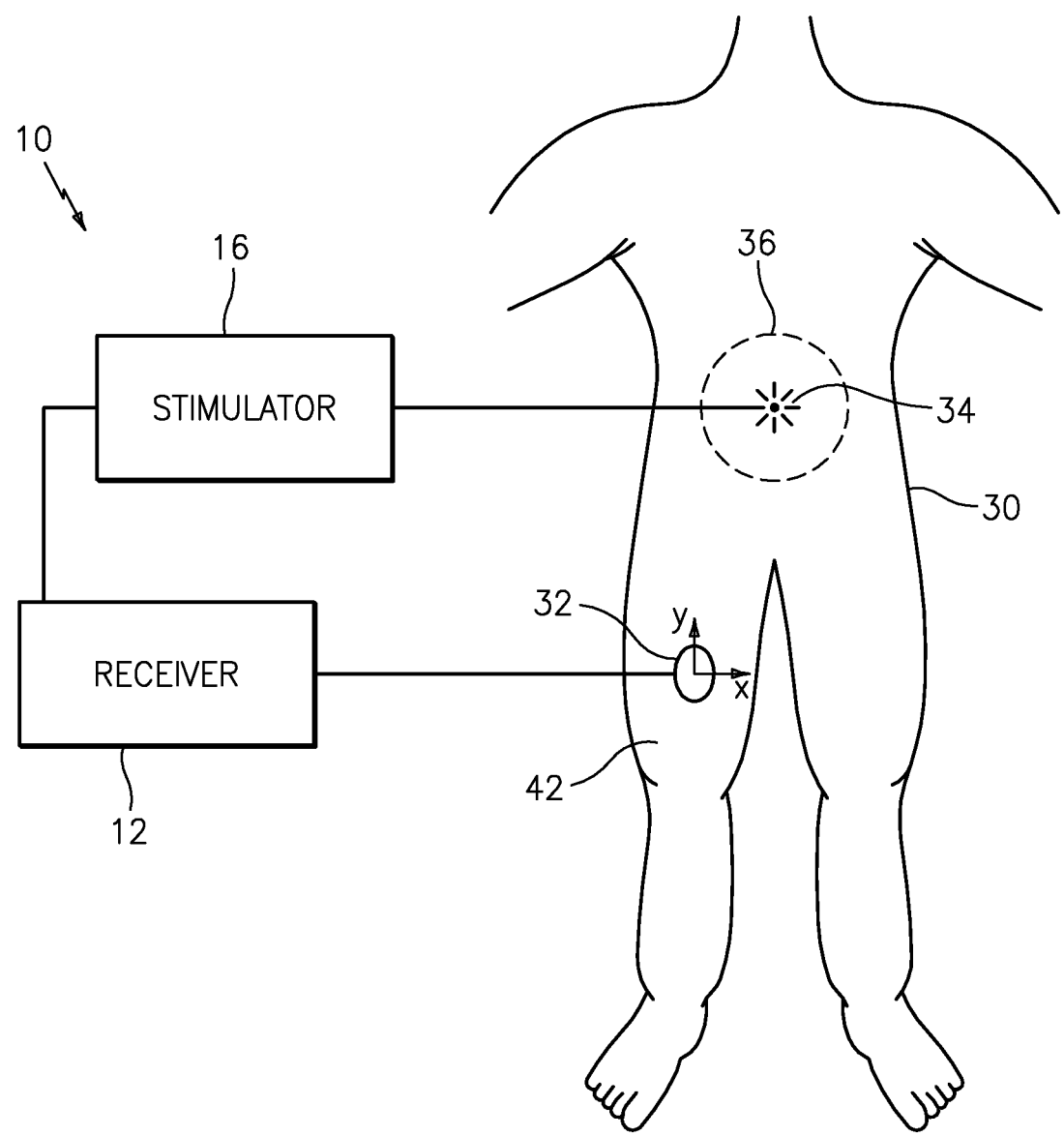
FIG. 2 is a schematic illustration of an embodiment of a neural monitoring system and a treatment area of a human subject.

FIG. 2 schematically illustrates an embodiment of a neural monitoring system 10 being used with a human subject 30. As shown, the neural monitoring system 10 includes a receiver 12, a stimulator 16, and a sensing device 32. The stimulator 16 may be configured to provide a stimulus 34 within a treatment region 36 of the subject 30. Exemplary treatment regions 36 may include the posterior, posterolateral, lateral, anterolateral or anterior regions of the sacral, lumbar, thoracic or cervical spine, as well as the tissue surrounding such regions. The stimulator 16 may be configured to provide the stimulus 34 constantly during a surgical procedure, or selectively at the discretion of the surgeon.

Figure 3:
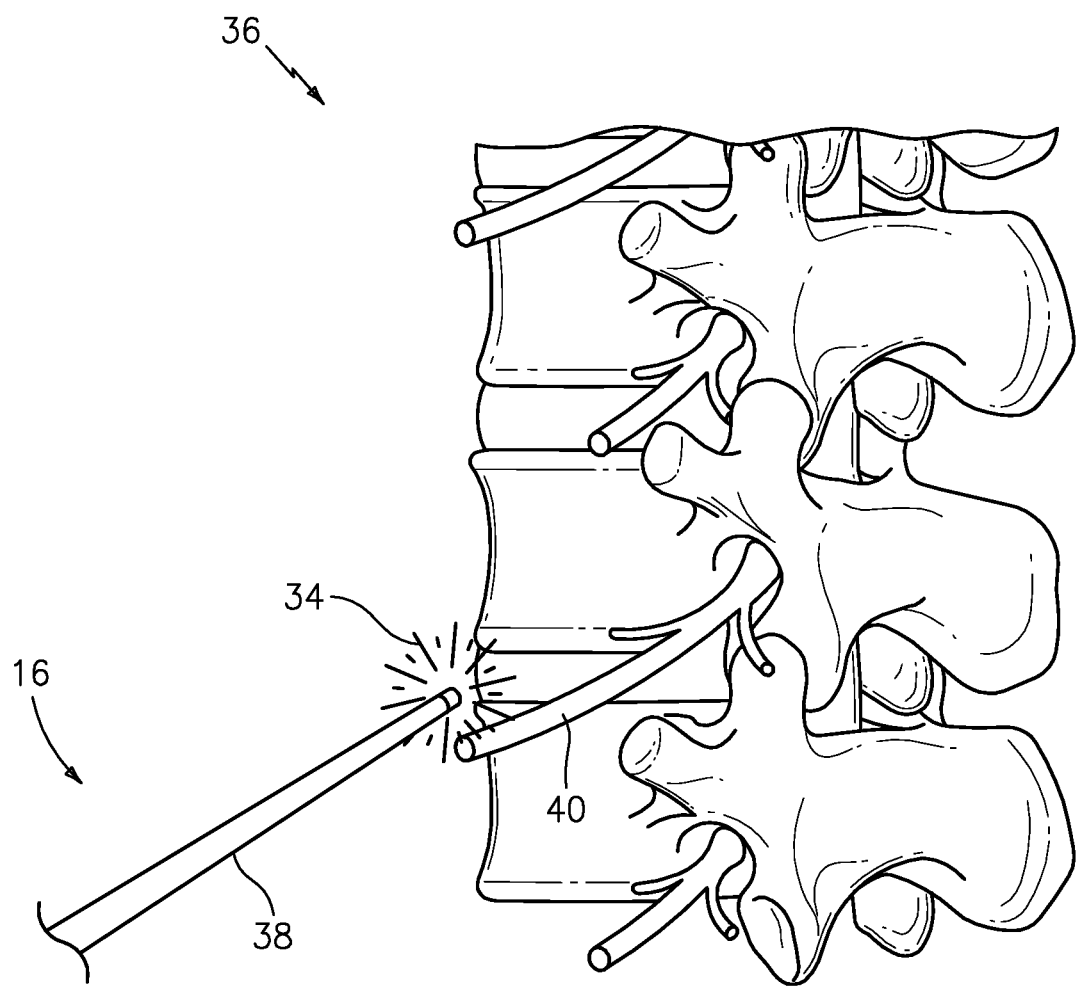
FIG. 3 is an illustration of a stimulator probe within a treatment area of a subject.

As shown in FIG. 3, in an embodiment, the stimulator 16 may include a probe 38 or other invasive medical instrument configured to extend within the treatment region 36 of the subject 30, and provide a stimulus 34 therein. The stimulus 34 may be, for example, an electrical stimulus, though may alternatively be a thermal, chemical, ultrasonic, or infrared stimulus, or may include a direct mechanical contact with the nerve. If the stimulus 34 is provided at or sufficiently close to a nerve within the treatment region 36 (e.g., nerve 40), the stimulus 34 may be received by the nerve in a manner that causes the nerve to depolarize. A depolarizing nerve may then induce a response in a muscle that is innervated by the nerve. Exemplary muscle responses may include, for example, physical motion, acceleration, displacement, or vibration of the muscle, and/or changes in muscle's electrical polarity. While FIGS. 2 and 3 illustrate the treatment region 36 including the lumbar spine, it is understood that the present invention may be used in connection with other surgical or therapeutic procedures that may be performed in the proximity of other peripheral motor nerves.

As generally illustrated in FIG. 2, the neural monitoring system 10 may include one or more sensing devices 32 that are configured to detect mechanical and/or electrical responses of various muscles of the subject 30. In an embodiment, a sensing device 32 may be affixed to the skin of the subject 30 in a manner that places it in communication with a particular muscle or muscle group innervated by a nerve within the treatment area 36. For example, as shown, the sensing device 32 may be placed in communication with a quadriceps muscle 42 of the subject 30. As used herein, the sensing device may be considered to be in communication with a muscle if it is sufficiently proximate to the muscle group to sense a mechanical and/or electrical parameter of the muscle. A sensed mechanical parameter may include, for example, muscle motion, acceleration, displacement, vibration, or the like. Likewise, a sensed electrical parameter may include an electrical potential of the muscle, such as when the innervated muscle is electrically or electrochemically activated.

Figure 4:
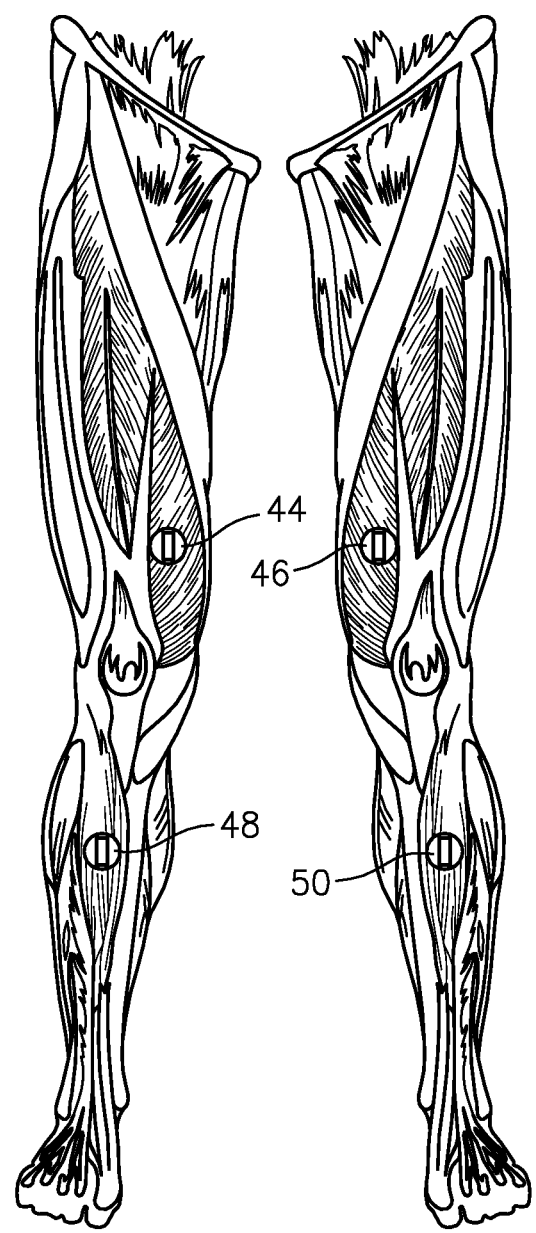
FIG. 4 is an illustration of an exemplary placement of a plurality of sensing devices.

By way of example, and not limitation, during a discectomy of the lumbar spine, a surgeon may know that the nerves exiting the L2, L3 and L4 foramen are potentially located in the treatment region 36. As illustrated in FIG. 4, the surgeon may place a sensing device 32 on each muscle innervated by those nerves. For instance, sensor devices 44, 46 may be placed on the vastus medialis muscles, which are innervated by nerves exiting the L2 and L3 foramen. Likewise sensors 48, 50 may be placed on the tibialis anterior muscles, which are innervated by the nerves exiting the L4 foramen. If a muscle response is then detected by one of these sensor devices, the surgeon may then be alerted accordingly.

Figure 5A:
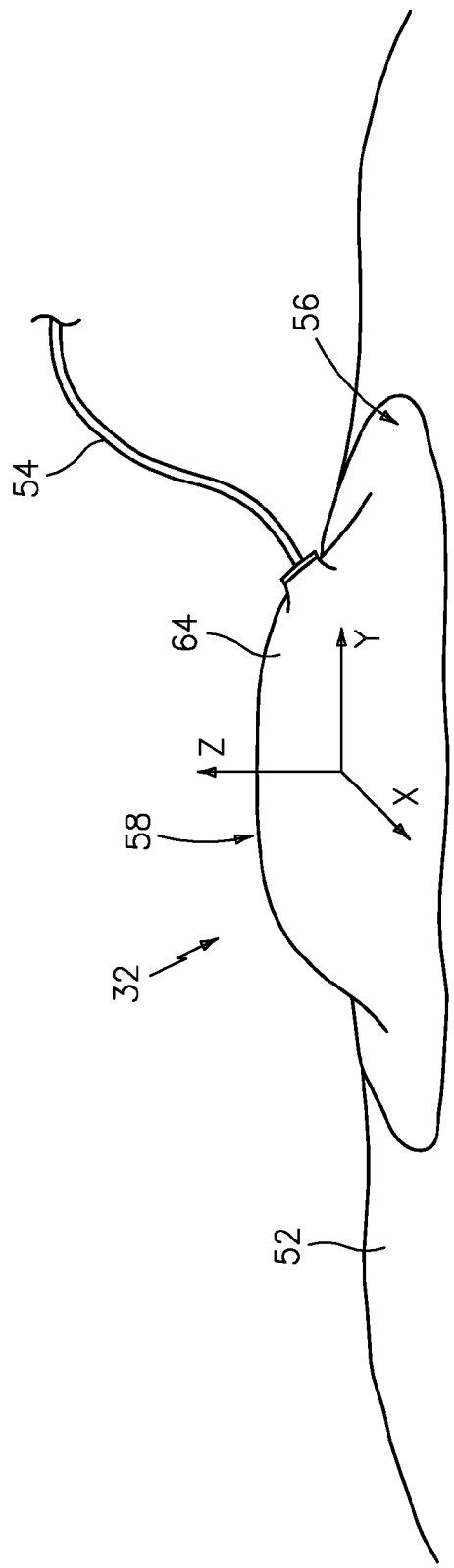
FIGS. 5A-5F are illustrations of various embodiments of a sensing device.
Figure 5B:
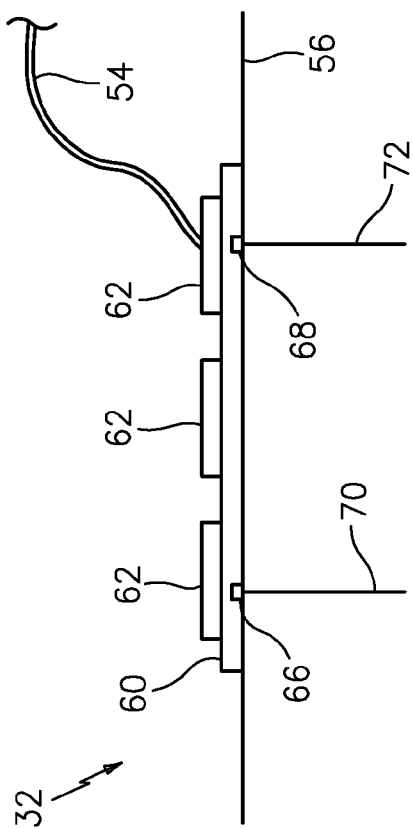

FIGS. 5A-5F illustrate various embodiments of a sensing device 32. As shown in FIG. 5A, the sensing device 32 may be affixed to the skin 52 of the subject 30 in such a manner that it is in mechanical and/or electrical communication with a particular muscle or muscle group of the subject (e.g., quadriceps muscle 42 as shown in FIG. 2). In an embodiment, the sensor device 32 may include a cable 54 configured to connect with an interface 20 of a receiver 12, an adhesive patch portion 56 that may adhere the sensor device to the skin 52 of the subject 30, and an instrument portion 58. As generally illustrated in FIG. 5B, the instrument portion 58 may include a circuit board 60 and one or more electrical components 62. In an embodiment, the circuit board 60 may be a rigid circuit board, such as one made from, for example, an FR-4 substrate. Alternatively, the circuit board 60 may be a flexible circuit board, such as one made from a polyimide, PEEK, polyester, or other flexible substrate. In an embodiment, as shown in FIG. 5A, the instrument portion 58 of the sensor device 32 may be enclosed by a protective cover 64 that may serve as a fluid barrier and protect the internal electrical components 62 from external moisture.

Figure 5C:
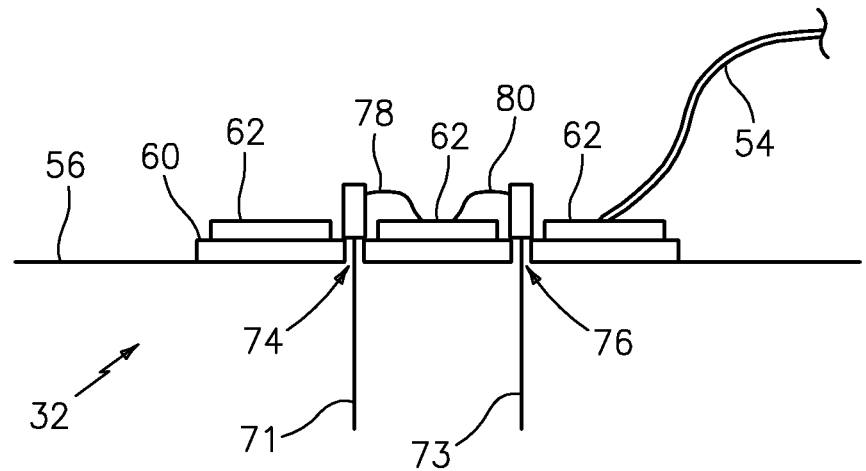

As illustrated in FIGS. 5B-5C, in an embodiment, the sensor device may have two or more surface electrodes 66, 68 and/or needle electrodes 70, 72 that are configured to be placed in electrical communication with the skin and/or muscle of the subject 30. In an embodiment, the surface electrodes 66, 68 may be configured to make electrical contact with the skin 52 of the subject 30 to monitor the electrical parameters of the adjacent muscle (e.g., quadriceps muscle 42) and/or to detect contact with the subject. Surface electrodes may require the surface of the skin to be shaved or coated with an electrically conducting gel to improve the electrical connectivity with the skin 52. Conversely, needle electrodes may penetrate the skin and extend directly into the muscle below.

As illustrated in FIG. 5B, the electrodes, such as needle electrodes 70, 72, may be integrated into the sensing device 32 in a fixed location and/or arrangement. Through the fixed attachment with the circuit board 60, each electrode 70, 72 may provide a respective electrical signal to the one or more electrical components 62 via the circuit board 60. As illustrated in FIG. 5C, in an embodiment, the sensor device 32 may be configured to accept removable needle electrodes 71, 73 that may pass through respective apertures 74, 76 in the circuit board 60, and may couple to the one or more electrical components 62 via respective brushes, contacts, slip rings, wires 78, 80 or other known electrical contact means.

Figure 5D:
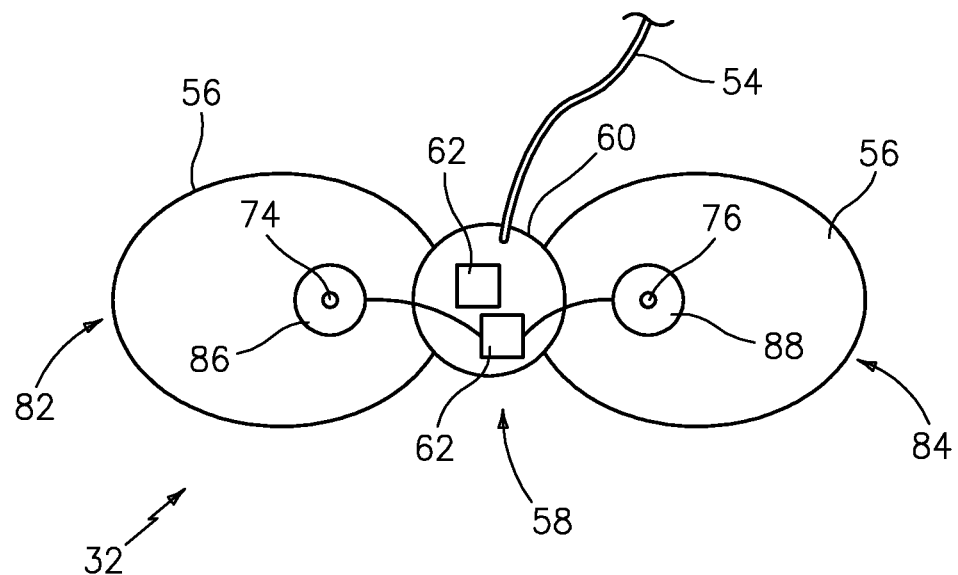

FIG. 5D illustrates another embodiment of a sensing device that includes a central instrument portion 58 and two adjacent adhesive portions 82, 84. The instrument portion 58 may include one or more electrical components 62 affixed to a circuit board 60, and each adhesive portion 82, 84 may include a respective adhesive patch 56, and/or one or more surface or needle electrodes. In an embodiment, each adhesive portion 82, 84 may include a respective aperture 74, 76 configured to receive a needle electrode (e.g., needle electrodes 71, 73). Additionally, in an embodiment, each adhesive portion 82, 84 may include an electrically conductive pad 86, 88 surrounding respective apertures 74, 76 that may be configured to make electrical contact with a needle electrode passing through the respective apertures.

Figure 5E:
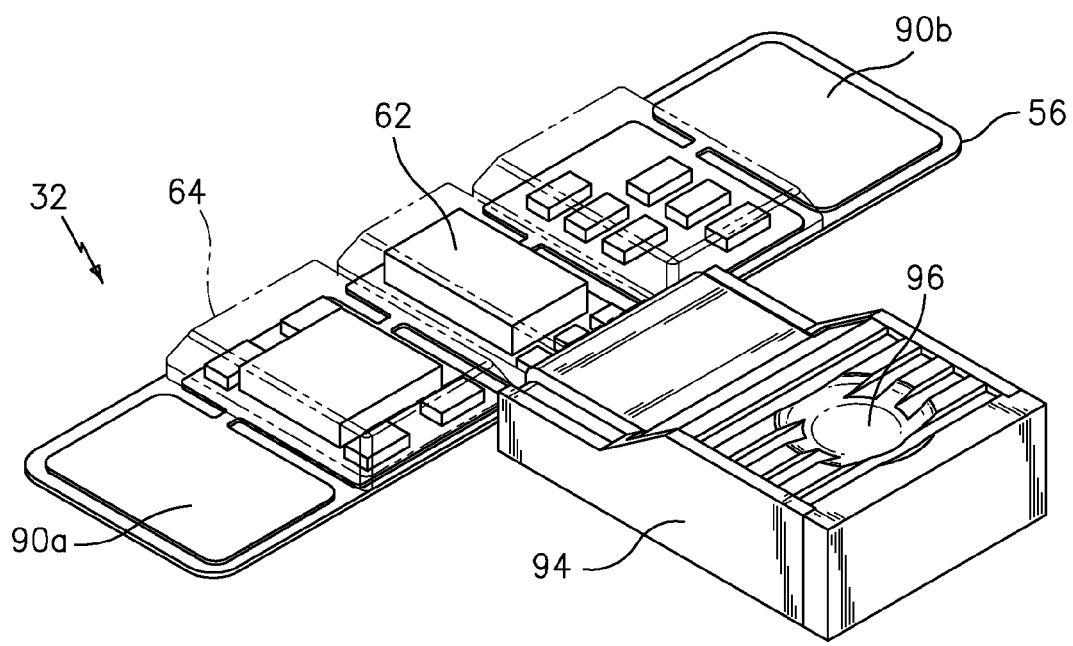
Figure 5F:
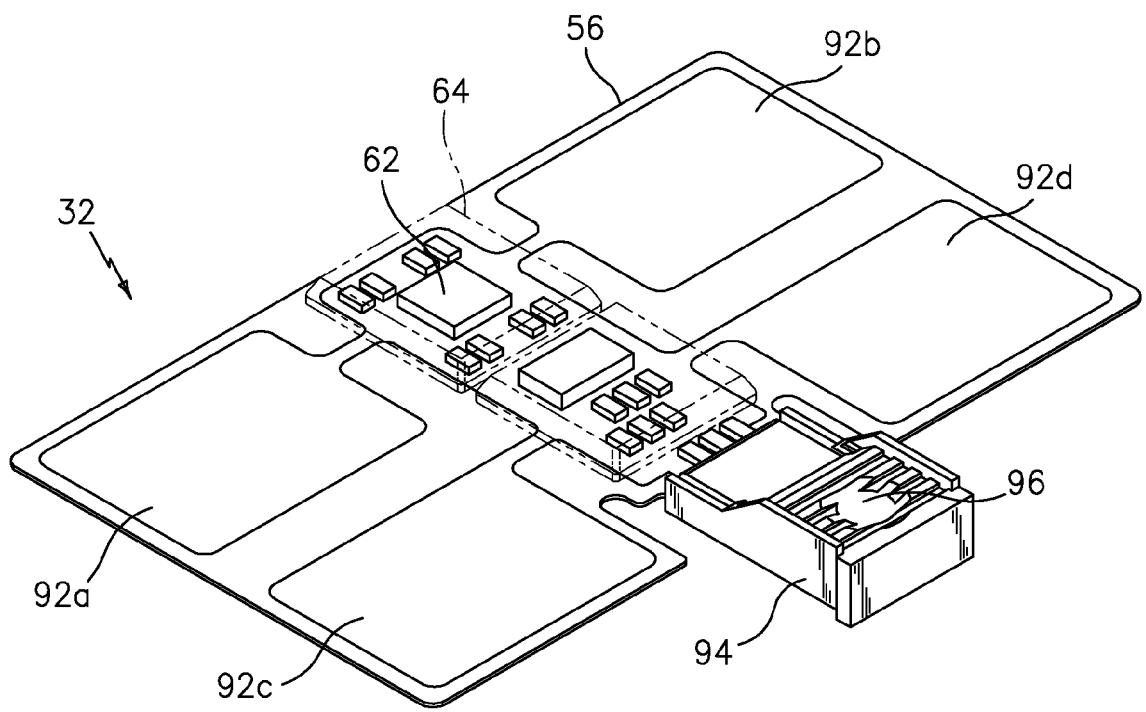

FIGS. 5E and 5F illustrate two further embodiments of a sensing device 32. In each embodiment, the sensing device 32 includes one or more electrical components 62 that are configured to sense one or more parameters of a muscle of a subject. In an embodiment, the electrical components 62 may include a mechanical sensor configured to detect and/or provide a signal corresponding to a mechanical movement of a muscle. An exemplary mechanical sensor may include an accelerometer designed to monitor motion in one or more axes. The one or more electrical components 62 may additionally be adapted to interface with a plurality of electrodes for the purpose of monitoring an electrical parameter of a muscle and/or detecting contact with the subject. Exemplary electrode configurations are illustrated in FIGS. 5E and 5F, (i.e., surface electrodes 90a, 90b, and surface electrodes 92a, 92b, 92c, 92d). As described above, the design of the sensing device 32 may be altered to accommodate needle electrodes in addition to, or instead of the surface electrodes.

In an embodiment where the sensing device 32 includes both a mechanical sensor and a plurality of electrodes, it may be beneficial to locate the mechanical sensor as close to the center of the device as possible. While not strictly necessary, such a configuration, as generally illustrated in FIGS. 5D-5F, may allow the greatest amount of adhesive material 56 to surround the mechanical sensor and thus improve its mechanical coupling with the skin.

The sensing device 32 may further be configured for stand-alone use, as generally shown in FIGS. 5E and 5F. In an embodiment, the sensing device 32 may include a local receiver module 94 that may receive the signals from the mechanical and/or electrical sensors and detect when a muscle event occurs. Additionally, the local receiver module 94 may be configured to provide an alert indication if such a muscle event is detected. In an embodiment, the indication may be provided by illuminating an associated light emitting diode (LED) 96, or alternatively by changing the color of an LED, such as from green to red. In another embodiment, the receiver module 94 may emit a sound that is indicative of a muscle movement. The receiver module 94 may be included with each sensor device 32 either by integrating it with the one or more electrical components 62, or by providing it as a detachable device similar to the module 94 shown in FIGS. 5E and 5F. The local receiver module 94 may further include a power source, such as a battery to provide power to the various electrical components.

In an embodiment, the local receiver module 94 may include all of the functionality and event detection capabilities of a more centralized receiver (such as the receiver 12 illustrated in FIG. 1). In a coordinated system that employs multiple sensors, each local receiver 94 may be configured to communicate alerts with a master receiver 12 using wired or wireless data communication means. In an embodiment, the master receiver 12 may aggregate the occurrence and/or timing of local events into a consolidated interface.

Figure 6:
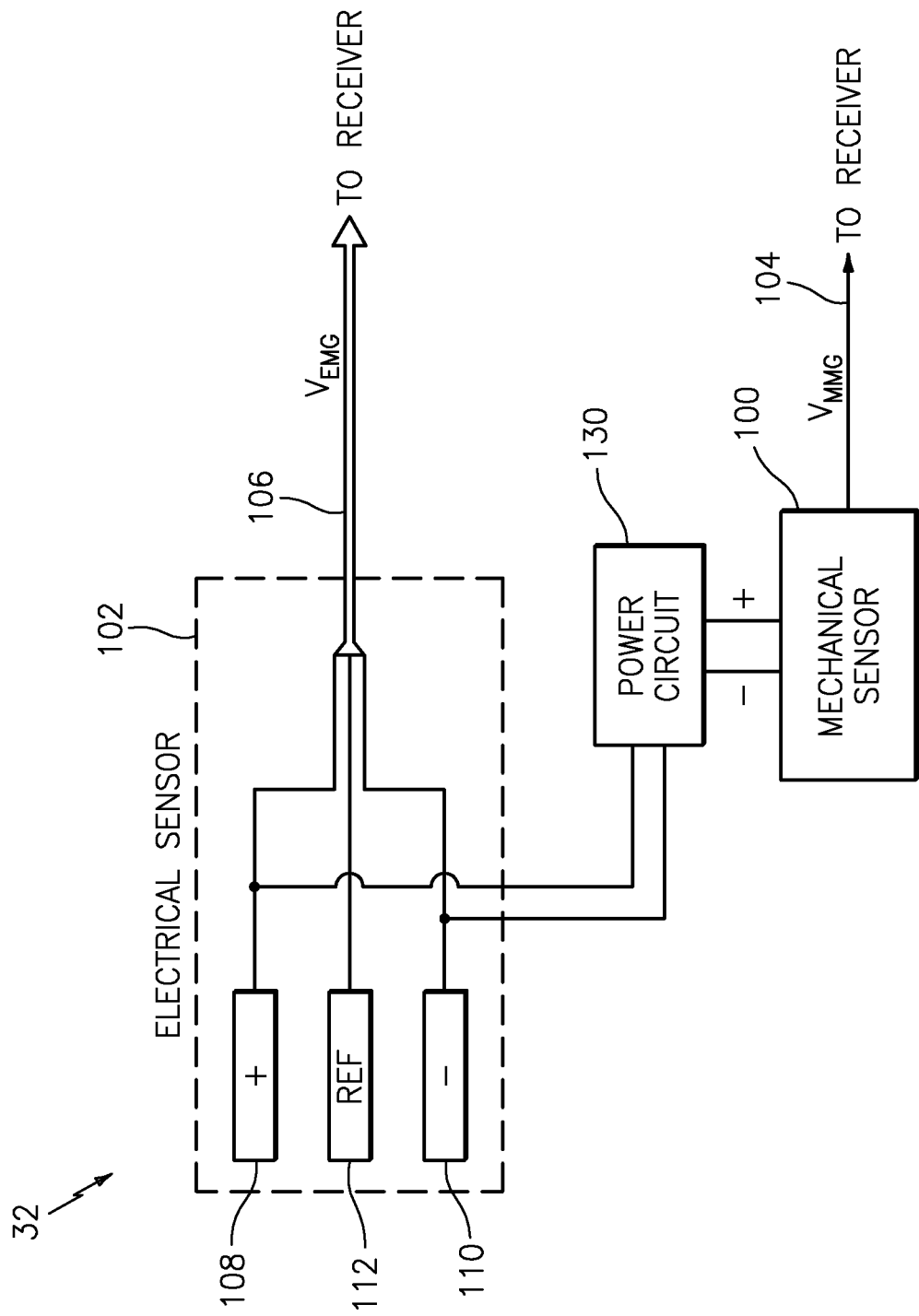
FIG. 6 is a schematic diagram of an embodiment of a sensing device.
Figure 7:
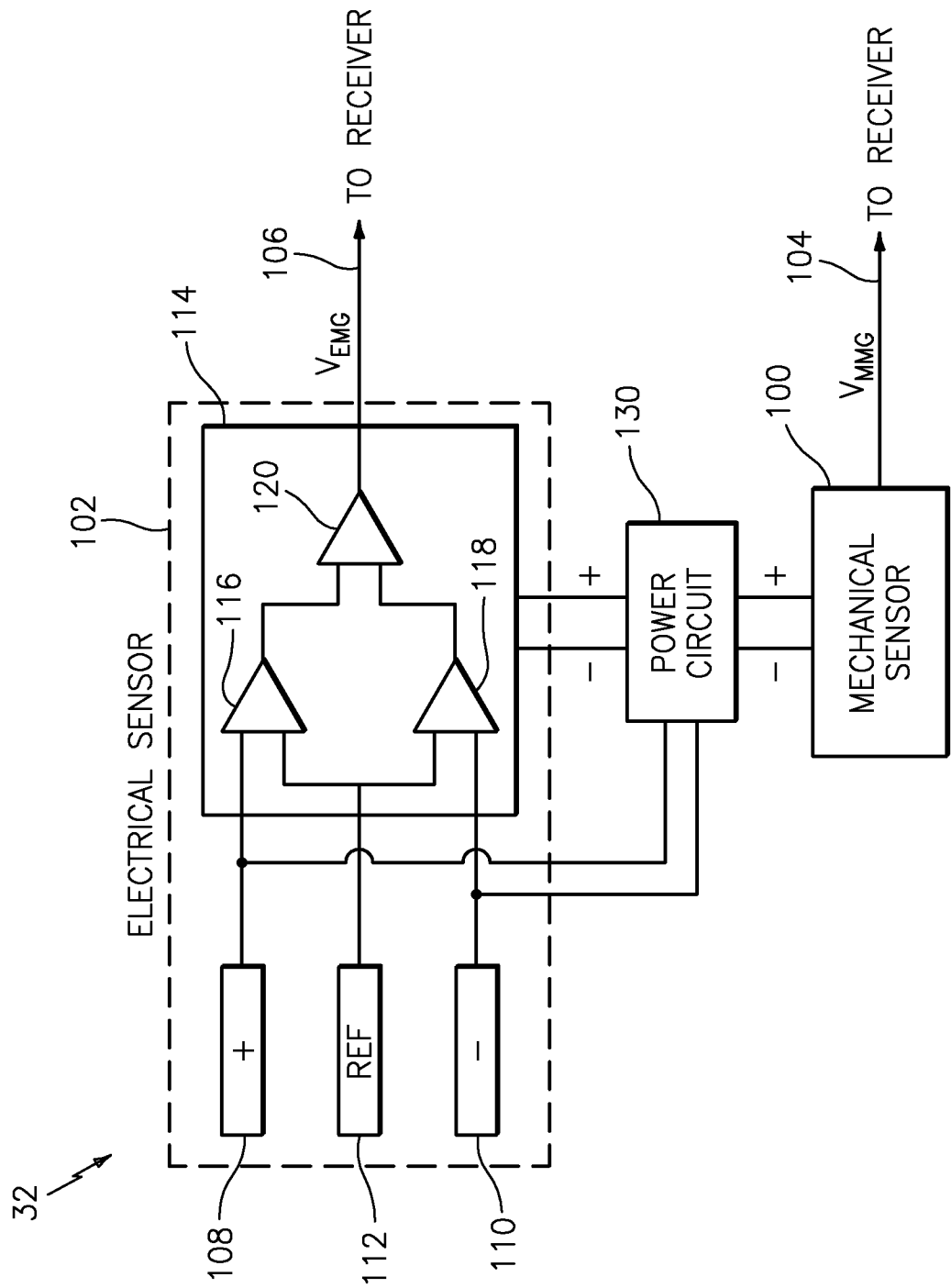
FIG. 7 is a schematic diagram of an embodiment of a sensing device.

FIGS. 6 and 7 illustrate electrical diagrams of various embodiments of a sensor device 32. These diagrams may generally represent the one or more electrical components 62 that are included with the device. In an embodiment, the sensor device 32 may include a mechanical sensor 100, and an electrical sensor 102. Each sensor may be configured to provide a respective output signal 104, 106 that may correspond to a parameter monitored by the sensor. Each output signal 104, 106 may be configured for either wired or wireless transmission to the receiver 12. In an embodiment, each output signal 104, 106 may include a respective voltage that corresponds to the monitored parameter. Alternatively, each output signal may include a variable current or a variable resistance signal that corresponds to the monitored parameter. For example, the output signal 104 from the mechanical sensor 100 may be a mechanomyography voltage signal ($V_{MMG}$), and the output signal 106 from the electrical sensor 102 may be an electromyography voltage signal ($V_{EMG}$). Each sensor 102, 104 may be configured to monitor for both triggered muscle responses (i.e., muscle responses that occur in response to a stimulator-applied stimulus 34) and for free-running muscle responses (i.e., muscle responses that may occur in the absence of a stimulator-applied stimulus 34).

In an embodiment, the mechanical sensor 100 may be configured to detect a mechanical response of the muscle or group of muscles that are in communication with the sensing device 32. The mechanical response may include, for example, muscle motion, acceleration, displacement, vibration, etc. In one exemplary approach, the mechanical sensor 100 may be an accelerometer configured to detect acceleration in at least one axis (e.g., in the direction normal to the surface of the skin, as represented by the z-axis in FIG. 5A). In an embodiment, the output signal 104 of the mechanical sensor 100 may be a voltage that corresponds to the sensed movement. The output signal 104 may indicate one or more directions, axes, and/or magnitudes, of motion, acceleration, displacement, or vibration experienced by mechanical sensor 100. In an embodiment, mechanical sensor 100 may be accelerometer model MMA7361 available from Freescale Semiconductor.

The electrical sensor 102 may be configured to detect an electrical response of the muscle or group of muscles that are in communication with the sensing device 32. The electrical sensor 102 may include a plurality of electrodes that are configured to be placed in communication with the muscle of the subject 30, either through the surface of the skin, or by extending through the skin and making direct contact with the muscle itself. The plurality of electrodes may include a first, "positive" electrode 108, and a second, "negative" electrode 110. Additionally, in an embodiment, the electrical sensor may include a reference electrode 112. The positive and negative electrodes 108, 110 may each monitor a polarity of a portion of the muscle that it is in communication with. The monitored polarity may be viewed with respect to a common reference electrode, such as electrode 112, which may be included with the sensing device 32 or may be separate from the device. In an embodiment, one single reference electrode may be used for a plurality of sensing devices, and may be included with the system as a distinct patch electrode, such as ground patch 18, illustrated in FIG. 1.

As illustrated in FIG. 6, in an embodiment, each electrode 108, 110, 112 of the electrical sensor 102 may pass an unfiltered, unamplified output signal directly to the receiver 12. In another embodiment, such as illustrated in FIG. 7, each electrode may first connect to a local amplification or isolation circuit 114. As illustrated, the amplification circuit 114 may compare the potentials monitored by each of the positive and negative electrodes 108, 110 with the potential monitored by a local reference electrode 112 using respective comparators 116, 118. These normalized signals may then be compared to each other through a third comparator 120, and the resulting output may be provided to the receiver 12 as a single output signal 106. Alternatively, if no local reference electrode exists, comparators 116 and 118 may be omitted and the positive and negative electrodes 108, 110 may feed directly into comparator 120. Comparator 120 may further be configured to amplify or boost the output signal 106 for transmission back to the receiver.

In an embodiment, as shown in FIG. 6, the sensing device 32 may further include a contact detection device, such as a power circuit 130 configured to monitor one or more electrodes (e.g., electrodes 108, 110), and energize the mechanical sensor 100 when contact with the subject 30 is detected. In an embodiment, as shown in FIG. 7, the power circuit 130 may also energize an amplification or isolation circuit 114 of the electrical sensor 102, if such a circuit is provided.

The power circuit 130 may, for example, include a capacitive switch that selectively provides power when a capacitance between the electrodes is at or below a certain threshold. Alternatively, the power circuit 130 may energize the sensor components when a threshold background or baseline electric field is detected. Alternatively, the power circuit 130 may energize the sensor components when a threshold background or baseline electrical signal is detected. The presence of such a background electrical activity (such as free-running EMG activity) may indicate that the sensor is in contact with the subject, as it does not exist apart from the subject. If such electrical activity is detected, the power circuit may act as a high impedance relay and provide power to the various components.

In an embodiment, the power circuit 130 may create an alert condition if contact with the subject 30 is lost. The alert condition may include the transmission (or lack thereof) of a separate contact signal to the receiver 12, or may include the absence of a mechanical output signal. For example, if the electrodes become decoupled from the subject 30, the baseline electrical activity or impedance sensed by the power circuit may disappear. Upon this drop-out, the power circuit 130 may switch off the supply power to the mechanical sensor 100 and cause the sensor 100 to stop transmitting a mechanical output signal 104. The receiver 12 may interpret the break in transmission as a loss of sensor contact, which may be conveyed to the user through an appropriate alert.

Figure 8:
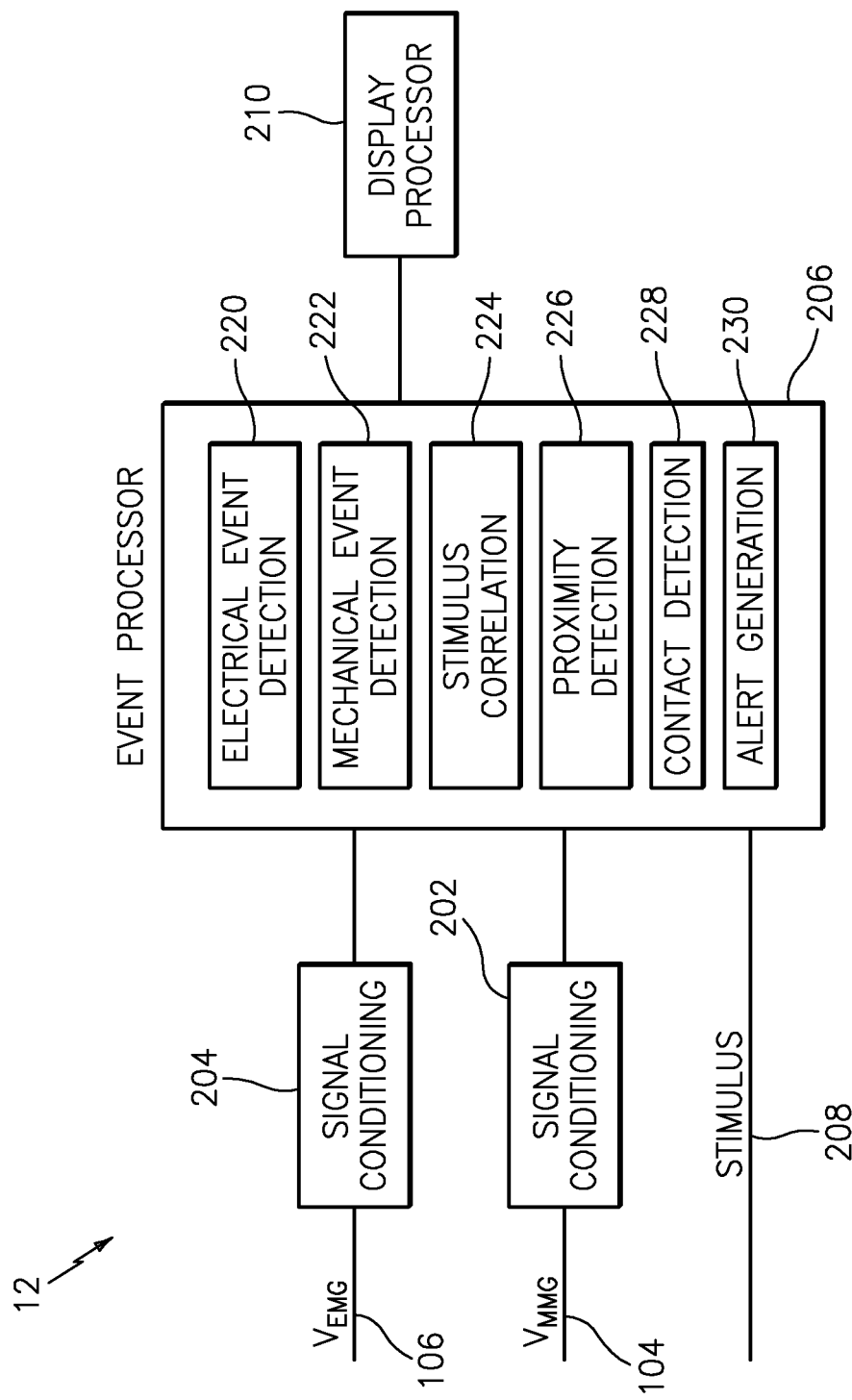
FIG. 8 is a schematic diagram of an embodiment of a receiver.

As described above, the sensing device 32 may provide an output signal (e.g. mechanical output signal 104 and/or electrical output signal 106) to a receiver 12 for processing. FIG. 8 illustrates a schematic representation of the receiver 12, which may be similar in function to a local receiver module 94. In an embodiment, the mechanical and/or electrical output signals 104, 106 may each pass through a respective signal conditioning circuit 200, 202, which may amplify the signal and/or filter out any unwanted noise. The filtered signals may then be received by an event processor 206 where they may be analyzed to determine their relationship to an applied stimulus 34. Additionally, the event processor 206 may be in communication with the stimulator 16 through a stimulus signal 208 for the purpose of correlating a detected event with an applied stimulus 34. The receiver 12 may further include a display processor 210 that is configured to provide graphical feedback to the user.

In an embodiment, the signal conditioning circuitry 202, 204 may include a band-pass filter that may filter out the DC component of the signals, along with any unwanted higher frequency components. In an exemplary embodiment, and without limitation, the filter may have a high-pass cutoff frequency in the range of 0.1-0.5 Hz, and may have a low-pass cutoff frequency in the range of 75-125 Hz.

The event processor 206 may analyze the filtered signals to, for example, detect the occurrence of an electrical event 220, detect the occurrence of a mechanical event 222, determine if a detected event corresponds to an applied stimulus 224, determine the proximity of a nerve from an applied stimulus 226, determine if a sensor has become disconnected from the subject 228, and/or determine if the surgeon should be provided with an alert 230.

Figure 9:
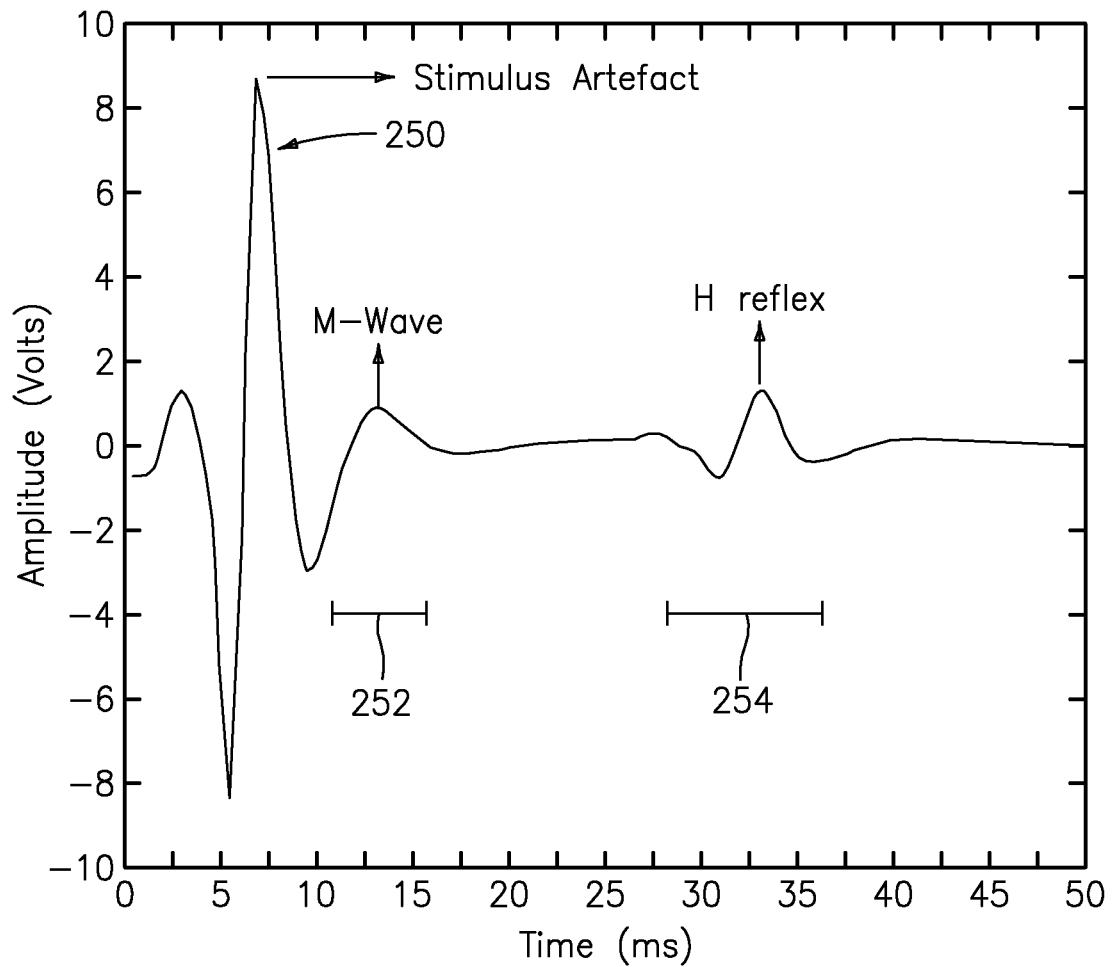
FIG. 9 is a graph of a electromyography response to an applied stimulus.

In an embodiment, as shown in FIG. 9, and exemplary electrical response to an applied pulse stimulus may include three components: a stimulus artefact 250, a muscle motor response 252 (also referred to as the "M-Wave"), and the Hoffmann Reflex 254 ("H-Reflex"). The stimulus artefact 250 may be a direct result of the applied electrical current within the body, and may not reflect a nerve's ability to transmit an action potential. Quite to the contrary, the M-Wave 252 is the action potential within a muscle that is caused by the depolarization of a nerve. This action potential is the primary cause of a natural mechanical motor response of a muscle, and is a result of the electrochemical activity of the motor neurons. Similar to the M-Wave 252, the H-Reflex 254 is a nerve-transmitted reflex response that may provide useful information about the presence or function of a nerve located proximate to the stimulator. In an embodiment, the receiver 12 may analyze the electrical output signal 106 to detect an M-Wave 252 or H-Reflex 254 electrical event. The system may then compare the magnitude of the detected electrical event with a pre-determined threshold to provide a general indication of proximity between the stimulator and a given nerve.

In practice, traditional systems may have difficulty differentiating the M-Wave 252 from the stimulus artefact 250 due to the duration and magnitude of the artefact and the close timing of the two events. To create a more robust detection system, the receiver 12 may analyze the mechanical sensor output 104 for the existence of mechanical events 222 and/or attempt to correlate the mechanical events with the electrical events. Because mechanical events are generally not susceptible to the stimulus artefact 250, they may be used to enhance the sensitivity and/or specificity of a purely electrical detection system.

Figure 10:
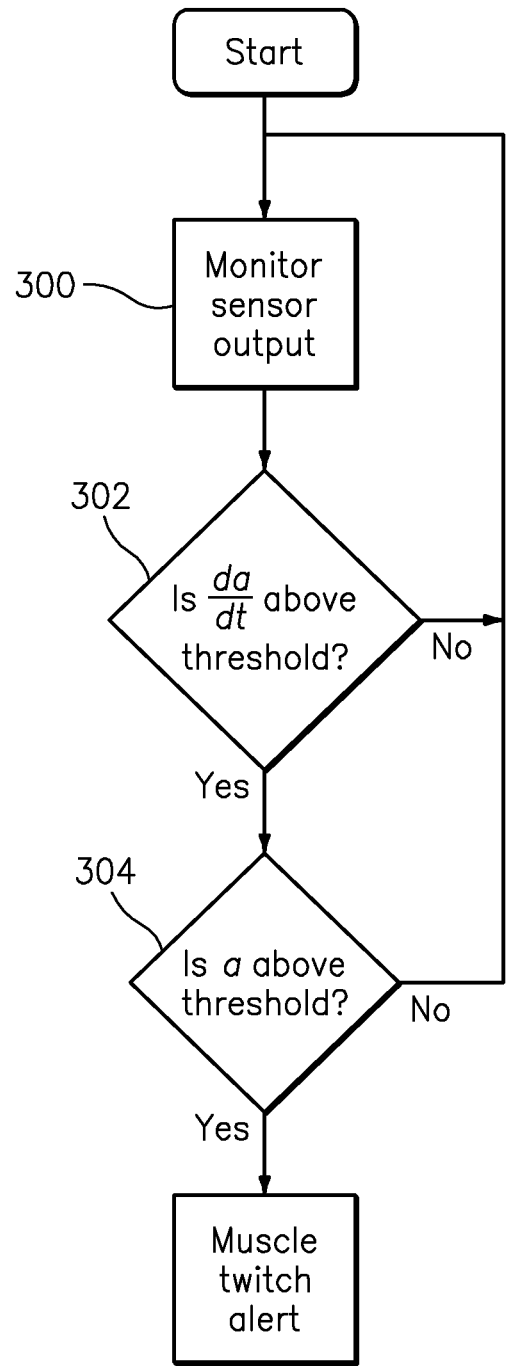
FIG. 10 is a flow chart illustrating an exemplary muscle response detection scheme.

In an exemplary embodiment, mechanical sensor 100 may comprise an accelerometer. As illustrated in FIG. 10, the receiver 12 may detect the existence of mechanical events 222 and/or correlate the events to an applied stimulus 224 by first registering raw readings from the accelerometer in step 300 (e.g., mechanical output signal 104). The system may then use these raw readings to derive the amount of muscle "jerk" experienced by the patient ("jerk," or a "jerk value," is the rate of change of the sensed acceleration (i.e. $da/dt$)). While a jerk value may be derived by taking the time derivative of acceleration, it may also be computed from other sensed mechanical parameters, such as velocity or position. It has been found that a muscle response induced by a provided stimulus may correspond to a particular jerk rate. By setting an appropriate threshold and comparing the derived jerk to the threshold (step 302), the system may be able to initially filter recorded readings to discriminate between a stimulator induced response, a patient-intended muscle movement, and an unintended environmental response (e.g. bumping the patient table). Finally, by comparing the amplitude of the sensed acceleration to a threshold (step 304), the system may determine whether the innervated nerve is sufficiently close to the stimulator to alert the physician. It should be understood that the jerk evaluation (step 302) may occur either before or after testing the amplitude of the sensed acceleration (step 304) without affecting the spirit of the invention.

Jerk and/or acceleration thresholds may be separately provided for each sensor at the discretion of the physician. In an embodiment where a local receiver 94 is included with each sensor device 32, such as illustrated in FIGS. 5E and 5F, the thresholds may be modified from a central control system, such as receiver 12, and remotely programmed into each device. In such an embodiment, local event detection may operate by monitoring the mechanical and/or electrical response of the proximate muscle according to the associated thresholds. A muscle twitch alert may comprise a visual or audible indication on the sensor itself if the individual thresholds are crossed and a muscle event is detected.

In an embodiment incorporating electrical stimulation, the system may further detect whether an electrical stimulus was transmitted immediately prior to a sensed response. This correlation may allow the system to further relate a sensed muscle response to the physician's actions. The system may use the stimulus correlation to alert the physician of a potentially applied manual stimulus (i.e., if a muscle response was detected in the absence of an electrical stimulus, the response may indicate a physical contact with, or manipulation of the nerve that innervates the responding muscle). In other embodiments, other sensed or derived parameters may be used for the purpose of identifying stimulator-induced muscle response, as well as for testing the magnitude of the induced response.

Figure 11A:
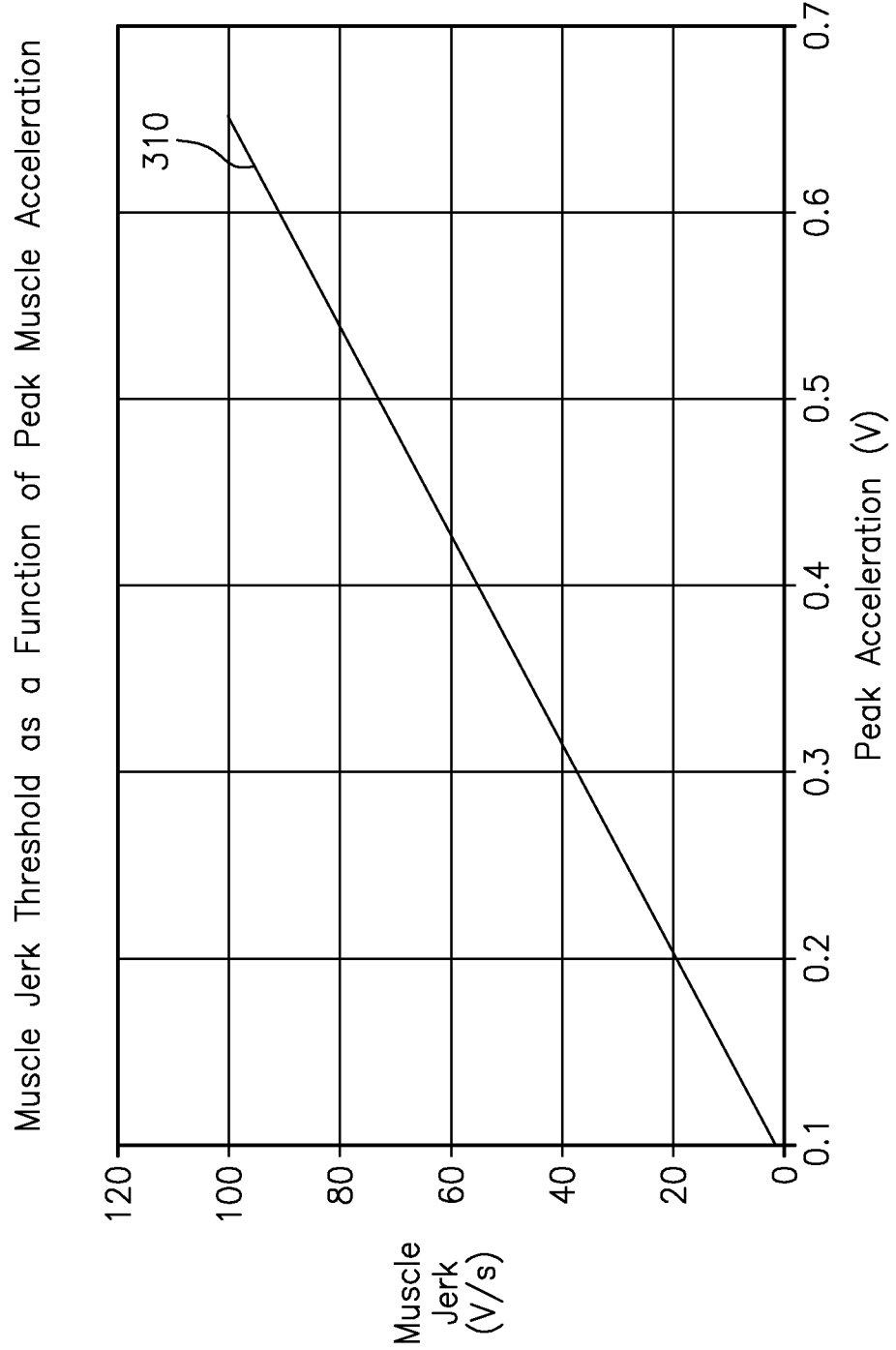
FIG. 11A is a graph illustrating an exemplary jerk threshold.
Figure 11B:
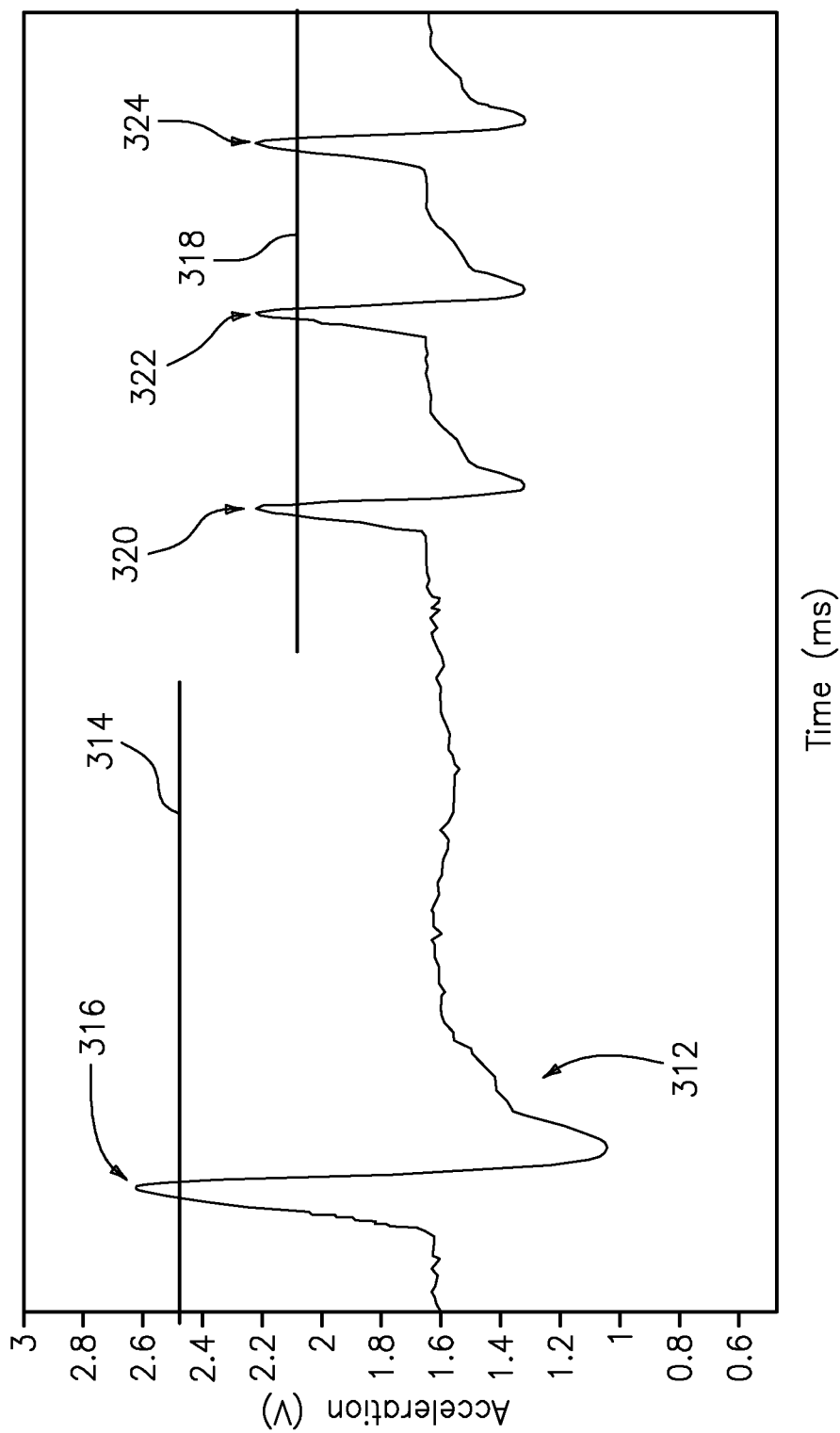
FIG. 11B is a graph illustrating an exemplary muscle response.

The thresholds used in steps 302 and 304 for detecting an event may be varied based on the type or timing of the detected sensor response. For example, in an embodiment, as generally shown in FIG. 11A, the jerk threshold 310 may be an increasing function of sensed accelerometer peak amplitude (in mV) In an embodiment, as generally illustrated in FIG. 11B, when analyzing an accelerometer output 312, a higher acceleration threshold 314 may be used for detecting a singular event (e.g., event 316), while a lower threshold 318 may be used for recurring events (e.g., events 320, 322, 324). Likewise, the system may use a lower acceleration threshold for events occurring within a specified time period following the application of a stimulus.

The above described system may be used to aid a physician in avoiding contact with a nerve. As described above, this may be accomplished by alerting the physician when he/she brings the stimulator within a certain proximity of a nerve. In another embodiment, the above described system may be used to aid a physician in locating a particular nerve, such as during a pain management procedure. As known in the art, certain pain management procedures require injecting a local anesthetic at, or in proximity of, a sensory nerve. By locating the motor nerve through the proximity detection methods described above, the physician may more accurately identify an injection site for the anesthetic.

Figure 12A:
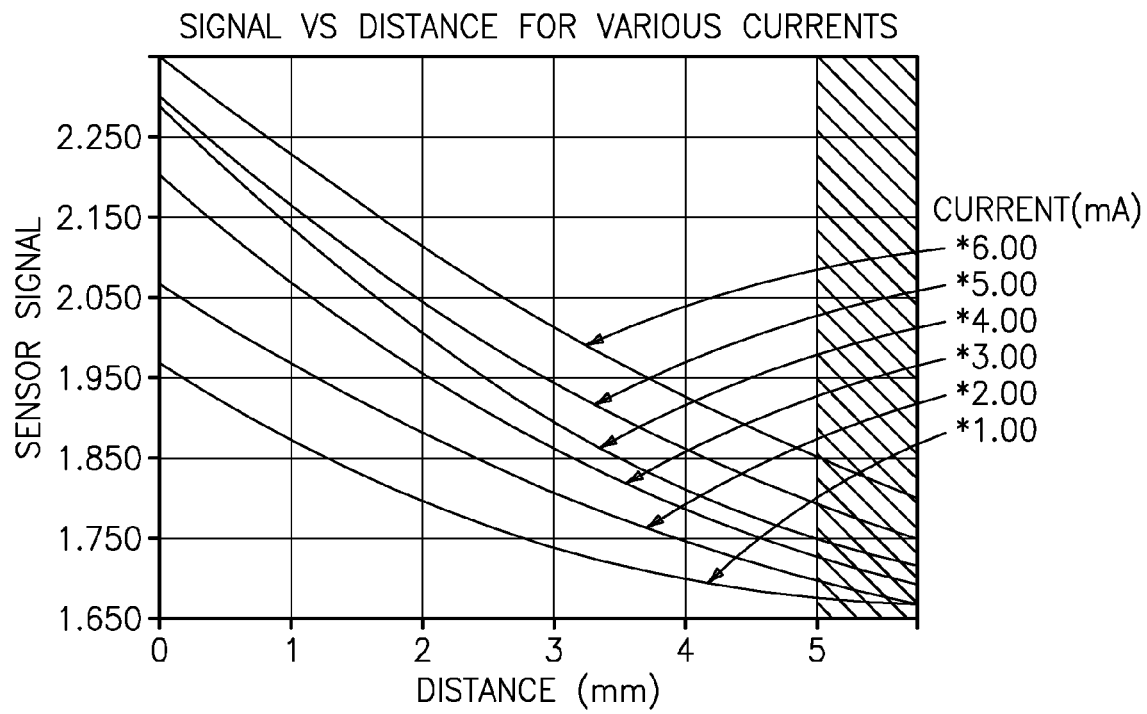
FIG. 12A is a graph illustrating an exemplary correlation between stimulator current, measured muscle response, and stimulator proximity to a nerve.
Figure 12B:
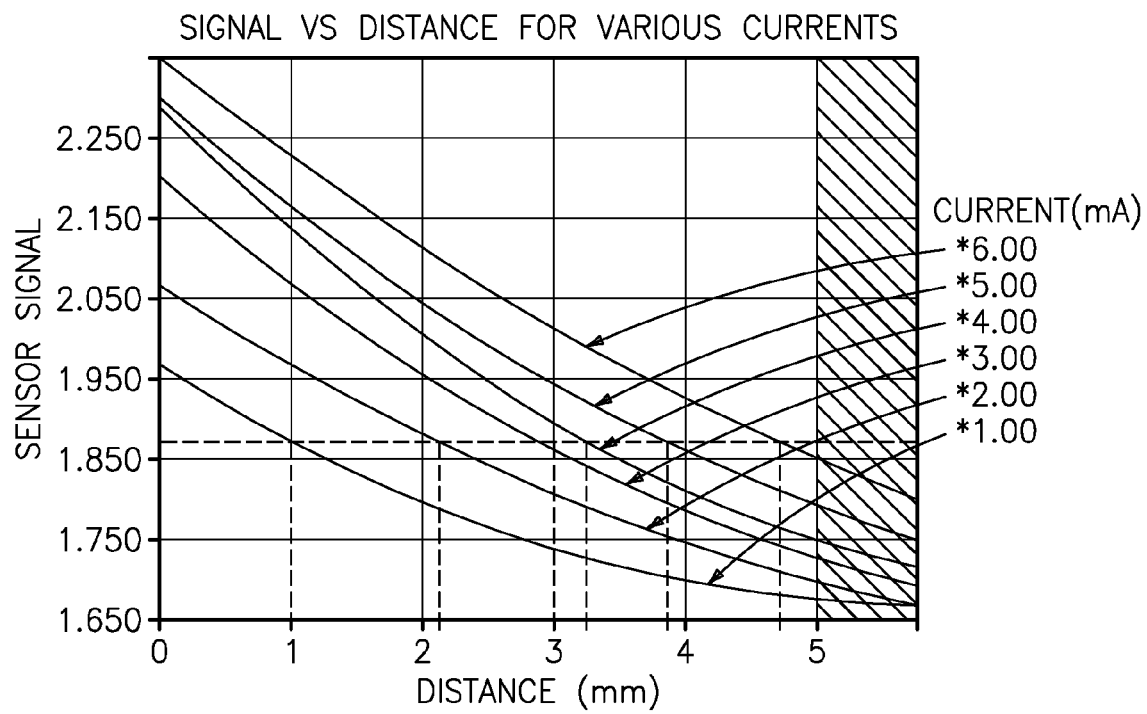
FIG. 12B is the graph of FIG. 12A including a desired threshold.

To further aid in neural proximity detection the receiver 12 may be configured to determine the proximity of a nerve from an applied stimulus 226 based on the electrical current of the applied stimulus and the measured mechanical sensor signal output. As generally shown in FIGS. 12a and 12b, correlation graphs may be used to provide the system or physician with an idea of the absolute proximity of the stimulator to the nerve. Correlation graphs, such as those shown in FIG. 12a, may be empirically determined on a patient-by-patient basis, or may be theoretically derived based on factors such as the thickness and density of the patient's skin, subcutaneous fat, and muscle. Alternatively, general correlation graphs such as illustrated in FIG. 12a may be generated, and provided with confidence bands or modified to suit a particular patient based on factors specific to the patient (e.g. body mass index).

In an exemplary approach, a physician may dictate the current level that is being applied to the stimulator, if the stimulator is close enough to a nerve to induce a muscle response, the sensing device 32 (such as illustrated in FIGS. 5-7) would generate an output signal corresponding to measured parameters, which may be quantified by the system. The system may use this knowledge of the stimulus strength and the magnitude of the mechanical sensor output signal 104 to determine an approximate absolute distance between the stimulator and the nerve In an embodiment, the system may have a pre-set initial current level that is selected based on the intended procedure. For example, when the software starts up the physician may be presented with a screen that inquiring as to either the type of surgical procedure being performed, or the distance away from the nerve the physician wishes to remain. The system may then use this information to adjust the threshold based on optimal current setting for the procedure or distance. The physician may also maintain the ability to vary the current level during the procedure.

As generally shown in the correlation graph of FIG. 12b, a threshold may be set within the range of expected sensor signal levels (e.g. as described in connection with FIG. 10 (step 304)). Once a particular sensor signal threshold is set, a physician may then select a static current based on his/her level of confidence with the procedure. For example, as described with reference to FIG. 12b, if the physician only wishes to only be alerted when he/she is within 3 mm of a nerve, given the pre-set threshold of approximately 1.86 units (e.g., volts), the physician would conduct the procedure with a 3 mA stimulus current. Alternatively, if the physician only desired to be alerted when within 1 mm of a nerve, he/she would conduct the procedure with a 1 mA current.

In an exemplary procedure, a physician may begin by setting a constant sensor threshold, and by setting the stimulator current near an upper end of a range. For example, as shown in FIGS. 12a and 12b, such a current value may be 6 mA. Using the known stimulus-response correlation, such as illustrated in FIGS. 12a and 12b, the system may provide an alert when the stimulator is within a particular distance of the nerve. In an embodiment, while maintaining the constant threshold, the applied current may be gradually decreased. By gradually dialing down this current, the physician may further refine his assessment of the nerve location. Similarly, the sensor threshold may be adjusted. For example, in an application where the physician wants more sensitivity, the threshold can be adjusted lower. Likewise, in an application where the physician wants more specificity, the threshold may be adjusted higher.

As further illustrated in the receiver 32 diagram of FIG. 8, in addition to being able to detect certain electrical and/or mechanical events 220, 222, correlate such events to a provided stimulus 224, and use the magnitude of the events to determine a nerve proximity from the applied stimulus 226, the event processor 206 may be configured to detect when a sensing device 32 loses contact with the subject 30. As described above, such a loss of contact may be determined based on a drop-out in the mechanical or electrical output signals 104, 106, as would be caused if a contact-based power circuit 130 ceased providing required power to the mechanical and/or electrical sensors 100, 102 (as illustrated, for example, in FIGS. 6 and 7). Alternatively, the event processor 206 may monitor the sensing device 32 for the presence of background electrical activity from the plurality of electrodes (e.g., electrodes 108, 110 in FIGS. 6 and 7). If contact between the electrodes and the subject 30 were lost, the background electrical activity (such as free-running electromyography activity) would cease, which may be interpreted by the processor as the loss of sensor contact. The event processor 206 may also be able to differentiate between background electrical activity when in contact with a subject and the background electrical activity in open air.

The event processor 206 may additionally generate alerts 230 that may correspond to sensed events, to stimulator proximity within a given threshold of a nerve, or to the loss of contact between a sensing device 32 and the subject 30. In an embodiment, the alerts may be visual in nature, and may be provided to a display processor 210 for display to a user. In an embodiment, the alerts may indicate to the user the location, magnitude, and/or nature of a detected event. In an embodiment, the display processor 210 may be integrated with the event processor 206 in a single general purpose processor or PC (for example as with computer 22 illustrated in FIG. 1). In an embodiment where event detection capabilities are included with the sensor, such as through a local receiver module 94, the alert generation module 230 may provide a visual and/or audible alert, such as through an on-board light or speaker, when a muscle event is detected.

During operation, the system 10 may be configured to provide a safe or "GO" signal if all sensing devices 32 are attached to the subject 30, the ground patch 18 is electrically coupled with the subject 30, and no muscle responses are detected. If the system detects that a sensing device 32 or ground patch 18 has lost contact with the subject 30, the system may be configured to alert the physician through an audible alert, or a visual alert such as a stop sign or "NO GO" warning. Such contact notification may similarly occur on the sensor itself, such as by illuminating a light with a color that corresponds with a loss of contact. In another embodiment, the sensor may provide an audible indication that it has lost contact with the subject. This warning may be used to convey that the neural monitoring system 10 is non-operational. Likewise, the receiver 12 may provide an indication to the user that may identify which sensor has lost contact. As described above, the system may also be configured to alert the physician if the entire system is operational and connected and a muscle response exceeds a threshold.

Therefore, a "GO" signal may represent a fully functioning system where a nerve is not proximate to the stimulator 16, while appropriate alternate warnings or alerts may further indicate that either the system is either non-operational and must be re-connected, or that a nerve is in proximity to the stimulator 16.

Figure 13A:
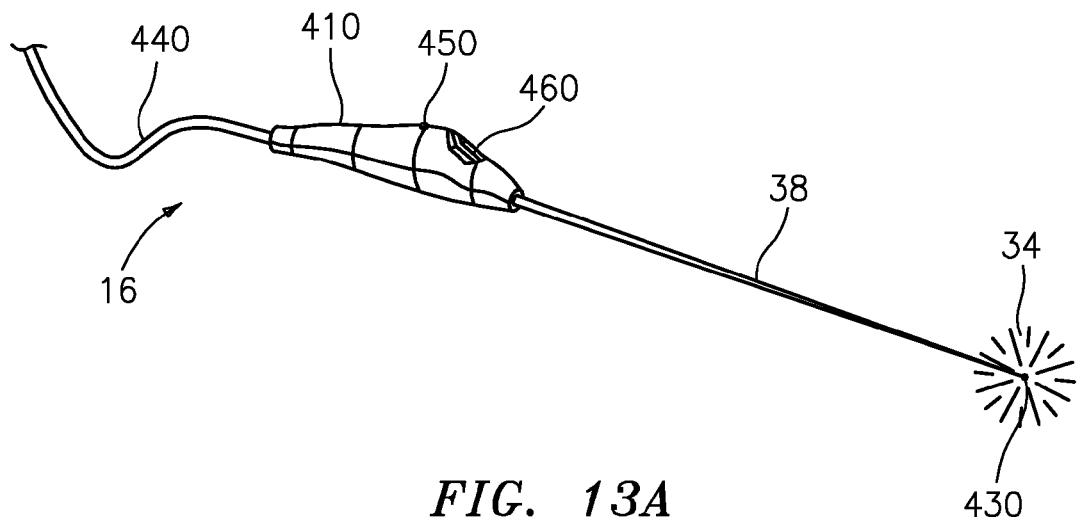
FIG. 13A is an illustration of an embodiment of a stimulator.
Figure 13B:
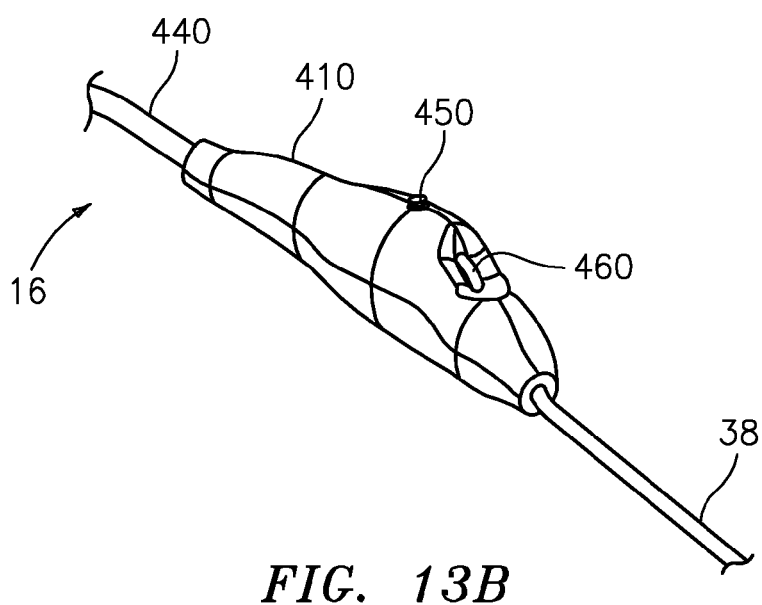
FIG. 13B is an enlarged view of the stimulator of FIG. 13A.

FIGS. 13A and 13B generally illustrate an embodiment of a stimulator 16, which may be similar to the stimulator 16 illustrated in FIG. 3, and configured for intrabody use. Stimulator 16 includes a handle 410, and a stimulator probe 38. In an embodiment, the stimulator probe 38 may be detachable from the stimulator handle 410, and may be replaceable with one or more different types of probes. In an embodiment, stimulator probe 38 includes an electrode 430 positioned at the distal end of the probe that may be configured to deliver a stimulus 34.

The stimulator handle 410 may be connected to an electrical cable 440 for transmitting signals between the receiver 12 and the stimulator 16. Handle 410 may include one or more buttons 450, selector devices, wheels 460, or LEDs. In an embodiment, a button, such as button 450, may be configured to selectively transmit an electrical stimulus 34 through stimulator probe 420. In an embodiment, rotation of wheel 460 may be configured to cycle through options on a display associated with the system, and the depression of wheel 460 may be configured to select an option on such a display. In an embodiment, rotation of wheel 460 may be configured to selectively vary the current intensity of the stimulus 34 transmitted through probe 38 and electrode 430. Additionally, visual indicators, such as LEDs may be incorporated into handle to convey information to the physician, such as, for example, detection of a muscle response or proximate nerve, a GO/NO-GO indicator, or may simply provide feedback to the physician that the stimulator is transmitting an electrical stimulus.

Figure 14:
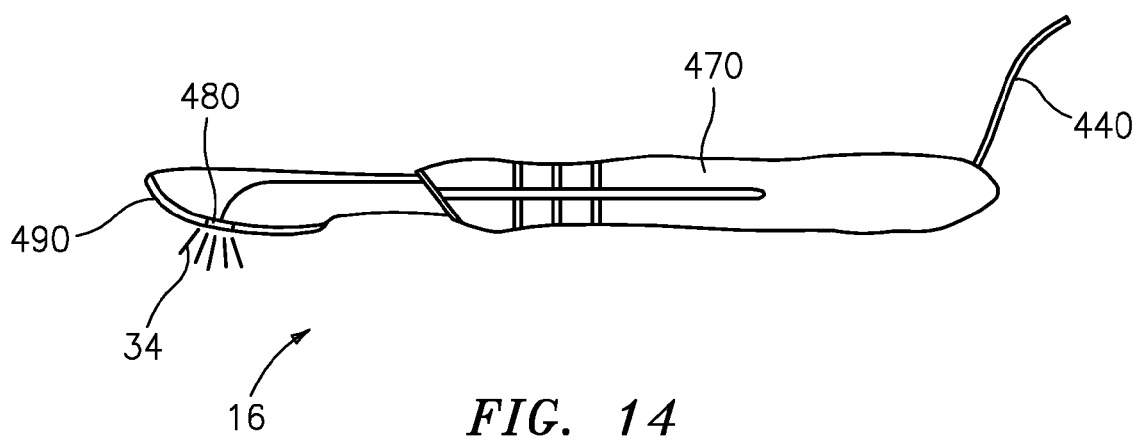
FIG. 14 is an illustration of an exemplary embodiment of a stimulator incorporated with an invasive medical device.

In an embodiment, stimulator 16 may be integrated with a medical device, such as scalpel 470 shown in FIG. 14. Other medical devices that may be adapted to include a stimulator may be, for example, forceps, suction devices, scissors, needles, retractors, clamps, screws, or other similar devices. In an exemplary embodiment, the scalpel 470 may include an electrode 480 that may be configured to provide a stimulus 34 to a portion of the subject. The electrode may be positioned in a location that may make first contact with the subject, such as the cutting edge 490.

Figure 15:
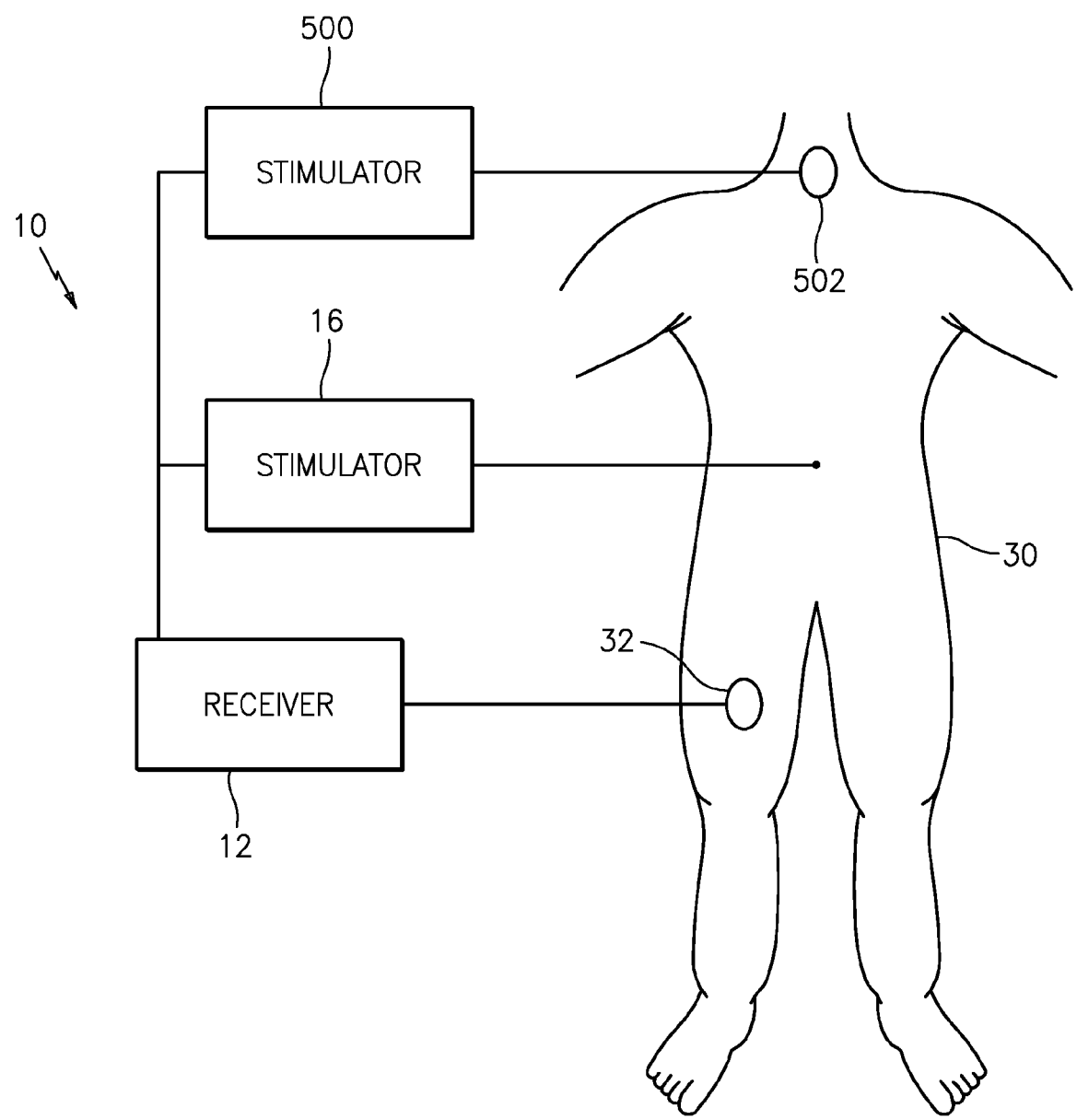
FIG. 15 is a schematic illustration of an embodiment of a neural monitoring system including a transdermal stimulator.

As generally illustrated in FIG. 15, the neural monitoring system 10 may further include a transdermal stimulator 500 that may provide a stimulus to a portion of the subject 30 through a stimulator patch 502. In an embodiment, the transdermal stimulator 500 may provide an electrical stimulus to the subject 30 through the use of surface or needle electrodes. In an exemplary use, a transdermal stimulator 500 may be positioned on the subject's scalp to stimulate the motor cortex in a transcranial fashion. By stimulating the motor cortex, the motor pathways of the pyramidal tracts may be excited, which may be sensed as a mechanical or electrical response within the subject's muscles. Such a technique may monitor motor evoked potentials (tcMEP) to evaluate the integrity of the subject's neural pathways, such as during procedures that may put the spinal column at risk. The transdermal stimulator 500 may be configured to deliver a transcranial stimulus on periodic basis; and, if an response is not detected by the one or more sensor devices 32 after the delivery of the stimulus, the receiver 12 may be configured to provide an alert to the user.

In another exemplary use, a transdermal stimulator 500 may be positioned on an extremity of a subject, and a sensing device may be positioned on the subject's scalp. Stimulating the extremity may evoke a somatosensory potential (SSEP) in the scalp that may be detected through an electrical sensor 102, and used to further evaluate the integrity of the subject's neural pathways. If a somatosensory potential is not sensed by a sensing device 32 after the generation of the stimulus, the receiver 12 may be configured to provide an alert to the user.

In an embodiment, the transdermal stimulator 500 may be a stand-alone stimulator patch, or may alternatively be integrated with the sensing device 32 to provide a stimulus through electrodes 108, 110 (as generally illustrated in FIGS. 6-7). If the transdermal stimulator 500 is integrated with the sensing device 32, tcMEP and SSEP responses may be intermittently tested without a need to reconfigure the neural monitoring system 10.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A neural monitoring system for determining a distance between a stimulator and a nerve within an intracorporeal treatment area of a human subject, with the nerve innervating a muscle, the neural monitoring system comprising:
   a stimulator configured to extend within the intracorporeal treatment area and to provide an electrical stimulus therein;
   a mechanical sensor configured to be placed in mechanical communication with the muscle and to generate a mechanomyography output signal corresponding to a sensed mechanical movement of the muscle; and
   a processor configured to:
      receive the mechanomyography output signal from the mechanical sensor;
      receive an indication of a magnitude of the provided intracorporeal stimulus;
      determine a magnitude of acceleration of the muscle from the received mechanomyography output signal;
      determine a distance between the stimulator and the nerve from the magnitude of the provided intracorporeal stimulus and the magnitude of acceleration of the muscle;
      wherein the processor is configured to determine the distance by selecting a distance value from a lookup table stored in a memory associated with the processor; and
      wherein the lookup table provides the distance value as a function of both a variable intracorporeal stimulus and a variable magnitude of acceleration of the muscle.

2. The neural monitoring system of claim 1, further comprising a display device in communication with the processor;
   wherein the processor is configured to determine if the sensed mechanical movement of the muscle was caused by the provided stimulus and
   wherein the processor is further configured to display an indication of the determined distance to a user via the display device if it is determined that the sensed mechanical movement of the muscle was caused by the provided stimulus.

3. The neural monitoring system of claim 1, wherein the processor is further configured to:
   compute a time derivative of an acceleration of the muscle from the mechanomyography output signal;
   compare the computed time derivative of acceleration to a jerk threshold; and
   indicate that the sensed mechanical movement of the muscle was induced by the provided intracorporeal stimulus if the computed time derivative of acceleration exceeds the jerk threshold.

4. The neural monitoring system of claim 2, wherein the processor is further configured to:
   compare the determined distance to a distance threshold; and
   wherein the indication is a first indication if the determined distance is less than the distance threshold; and
   wherein the indication is a second indication if the determined distance is greater than the distance threshold.

5. The neural monitoring system of claim 1, wherein the stimulator is an invasive medical instrument.

6. The neural monitoring system of claim 5, wherein the invasive medical instrument is a retractor.

7. The neural monitoring system of claim 5, wherein the invasive medical instrument is a screw.

8. The neural monitoring system of claim 1, wherein the mechanical sensor is in wireless data communication with the processor.

9. A method of determining a distance between a stimulator and a nerve within an intracorporeal treatment area of a human subject, with the nerve innervating a muscle, the method comprising:
   providing an electrical stimulus within the intracorporeal treatment area from a stimulator configured to extend within the intracorporeal treatment area;
   receiving a mechanomyography output signal from a mechanical sensor in mechanical communication with the muscle, the mechanomyography output signal corresponding to a mechanical movement of the muscle sensed by the mechanical sensor;
   receiving an indication of a magnitude of the provided intracorporeal stimulus;
   determining a magnitude of acceleration of the muscle from the received mechanomyography output signal;
   determining a distance between the stimulator and the nerve from the magnitude of the provided intracorporeal stimulus and the magnitude of acceleration of the muscle;
   wherein determining the distance includes selecting a distance value from a lookup table stored in a memory associated with the processor; and
   wherein the lookup table provides the distance value as a function of both a variable intracorporeal stimulus and a variable magnitude of acceleration of the muscle.

10. The method of claim 9, further comprising
    determining if the sensed mechanical movement of the muscle was caused by the provided stimulus; and
    displaying an indication of the determined distance to a user via a display device if it is determined that the sensed mechanical movement of the muscle was caused by the provided stimulus.

11. The method of claim 9, further comprising:
    computing a time derivative of an acceleration of the muscle from the mechanomyography output signal;
    comparing the computed time derivative of acceleration to a jerk threshold; and
    indicating that the sensed mechanical movement of the muscle was induced by the provided intracorporeal stimulus if the computed time derivative of acceleration exceeds the jerk threshold.

12. The method of claim 10, further comprising:
    comparing the determined distance to a distance threshold; and
    wherein the indication is a first indication if the determined distance is less than the distance threshold; and
    wherein the indication is a second indication if the determined distance is greater than the distance threshold.

13. The method of claim 10, further comprising:
    comparing the determined distance to a distance threshold; and
    injecting a local anesthetic within the treatment area if the determined proximity is less than the distance threshold and the sensed mechanical movement of the muscle was caused by the provided stimulus.

14. The system of claim 1, wherein the distance is expressed in millimeters.

* * * * *

UNITED STATES PATENT AND TRADEMARK OFFICE
CERTIFICATE OF CORRECTION

| | | |
|---|---|---|
| PATENT NO. | : 8,979,767 B2 | Page 1 of 1 |
| APPLICATION NO. | : 13/676809 | |
| DATED | : March 17, 2015 | |
| INVENTOR(S) | : Stephen Bartol and Christopher Wybo | |

It is certified that error appears in the above-identified patent and that said Letters Patent is hereby corrected as shown below:

In the Claims

Column 14, line 62:

The word "proximity" should be replaced with the word "distance" so that line 62 should read: "determined distance is less than the distance threshold".

Signed and Sealed this
Fifteenth Day of September, 2015

Michelle K. Lee
*Director of the United States Patent and Trademark Office*